(12) United States Patent
Dale

(10) Patent No.: US 7,160,547 B2
(45) Date of Patent: Jan. 9, 2007

(54) STREPTOCOCCAL STREPTOLYSIN S VACCINES

(75) Inventor: James B Dale, Memphis, TN (US)

(73) Assignee: University of Tennessee Research Corporation, Knoxville, TN (US)

( * ) Notice: Subject to any disclaimer, the term of this patent is extended or adjusted under 35 U.S.C. 154(b) by 36 days.

(21) Appl. No.: 10/268,336

(22) Filed: Oct. 9, 2002

(65) Prior Publication Data

US 2003/0157122 A1 Aug. 21, 2003

Related U.S. Application Data

(63) Continuation-in-part of application No. 09/975,455, filed on Oct. 10, 2001, now abandoned.

(60) Provisional application No. 60/239,432, filed on Oct. 10, 2000.

(51) Int. Cl.
*A61K 39/00* (2006.01)
*A61K 39/02* (2006.01)
*A61K 38/00* (2006.01)
*C07K 16/00* (2006.01)

(52) U.S. Cl. .............................. 424/185.1; 424/184.1; 424/185.1; 530/300; 530/388.2

(58) Field of Classification Search ............. 424/184.1, 424/185.1; 530/300, 388.1
See application file for complete search history.

(56) References Cited

U.S. PATENT DOCUMENTS

| 5,229,490 A | 7/1993 | Tam ........................... 530/324 |
| 5,580,563 A | 12/1996 | Tam ...................... 424/197.11 |
| 6,063,386 A | 5/2000 | Dale et al. ................ 424/244.1 |

FOREIGN PATENT DOCUMENTS

WO  WO 99/49049  * 9/1999

OTHER PUBLICATIONS

Dale et al, Vaccine 1996, vol. 14, No. 10.*
Dale et al, Vaccine 17, 1999, 193-200.*
Thomas E. Creighton, in his book, "Proteins: Structures and Molecular Properties, 1984", (pp. 314-315).*
Thomas E. Creighton, in his book "Protein Structure: A Practical Approach, 1989, pp. 184-186".*
Nosoh, Y. et al in "Protein Stability and Stabilization through Protein Engineering, 1991" (chapter 7, p. 197, second paragraph).*
Dale et al., Vaccine, 1996, vol. 14, No. 10.*
Thomas E. Creighton, in his book, "Proteins: Structures and Molecular Properties, 1984".*
Thomas E. Creighton, in his book "Protein Structure: A Practical Approach, 1989; pp. 184-186".*
Nosoh, Y. et al in "Protein Stability and Stabilization through Protein Engineering, 1991" (chapter 7, p. 197, second paragraph).*
Dale et al, Vaccine 1996, vol. 14, No. 10.*

Dale, J.B., "Group A Streptococcal Vaccines," *Infectious Disease Clinics of North America* 13(1):227-243, Mar. 1999.
Dale, J.B., "Antibodies against a Synthetic Peptide of SagA Neutralize the Cytolytic Activity of Streptolysin S from Group A Streptococci," *Infection and Immunity* 70(4): 2166-2170, Apr. 2002.
Alouf and Loridan, "Production, Purificatio, and Assay of Streptolysin S," *Methods in Enzymology* 165: 59-64, 1988.
Beachey et al., "Type-specific protective immunity evoked by synthetic peptide of *Streptococcus pyogenes* M protein," *Nature* 292: 457-459, Jul. 30, 1991.
Bernheimer, A. W., "Physical Behavior of Streptolysin S," *Journal of Bacteriology* 93(6):2024-2025, Jun. 1967.
Betschel et al., "Reduced Virulence of Group A Streptococcal Tn916 Mutants That Do Not Produce Streptolysin S," *Infection and Immunity* 66(4): 1671-1679, Apr. 1998.
Cunningham, M.W., "Pathogenesis of Group A Streptococcal Infections," *Clinical Microbiology Reviews* 13(3):470-511, Jul. 2000.
Dale et al., "Heterogeneity of Type-Specific and Cross-Reactive Antigenic Determinants within a Single M Protein of Group A Streptococci," *The Journal of Experimental Medicine* 151: 1026-1038, 1980.
Dale et al., "Recombinant, octavalent group A streptococcal M protein vaccine," *Vaccine* 14(10):944-948, 1996.
Dale and Beachey, "Localization of Protective Epitopes of the Amino Terminus of Type 5 Streptococcal M Protein," *Journal of Experimental Medicine* 163: 1191-1202, May 1986.
Dawson et al., "Synthesis of Proteins by Native Chemical Ligation," *Science* 266: 776-779, Nov. 4, 1994.
Fitzmaurice et al., "The assembly and immunological properties of non-linear synthetic immunogens containing T-cell and B-cell determinants," *Vaccine* 14(6): 553-560, 1996.
Francis et al., "Non-responsiveness to a foot-and-mouth disease virus peptide overcome by addition of foreign helper T-cell determinants," *Nature* 330: 168-170, Nov. 12, 1987.
Ginsburg, I., "Is streptolysin S of group A streptococci a virulence factor?" *APMIS* 107: 1051-1059, 1999.
Hryniewicz and Pryjma, "Effect of Streptolysin S on Human and Mouse T and B Lymphocytes," *Infection and Immunity* 16(3): 730-733, Jun. 1977.
Jackson et al., "Preparation and properties of totally synthetic immunogens," *Vaccine* 18: 355-361, 2000.
Jackson et al., "Free radical induced polymerization of synthetic peptides into polymeric immunogens," *Vaccine* 15(15): 1697-1705, 1997.

(Continued)

*Primary Examiner*—Nita Minnifield
*Assistant Examiner*—Vanessa L. Ford
(74) *Attorney, Agent, or Firm*—Seed IP Law Group PLLC

(57) ABSTRACT

Provided are streptolysin S (SLS) polypeptides, peptides, and variants thereof, antibodies directed thereto, and isolated nucleic acids encoding such proteins. In one embodiment, a method is provided wherein a synthetic peptide of SLS is used to elicit an immune response specific for SLS in a subject to treat or prevent a streptococcal infection. In other embodiments, antibodies that neutralize the hemolytic activity of the SLS toxin may be used as a vaccinating agent.

21 Claims, 1 Drawing Sheet

OTHER PUBLICATIONS

Kehoe et al., "Nucleotide Sequence of the Streptolysin O (SLO) Gene: Structural Homologues between SLO and Other Membrane-Damaging, Thiol-Activated Toxins," *Infection and Immunity 55*: 3228-3232, Dec. 1987.

Leclerc et al., "A synthetic vaccine constructed by copolymerization of B and T cell determinants," *Eur. J. Immunol. 17*:269-273, 1987.

Nizet et al., "Genetic Locus for Streptolysin S Production by Group A Streptococcus," *Infection and Immunity 68*(7): 4245-4254, Jul. 2000.

O'Brien-Simpson et al., "Polymerization of Unprotected Synthetic Peptides: A View toward Synthetic Peptide Vaccines," *J. Am. Chem. Soc. 119*: 1183-1188, 1997.

Ofek et al., "Oxygen-Stable Hemolysins of Group A Streptococci," *Infection and Immunity 6*(4): 459-464, Oct. 1972.

Rose, K., "Facile Synthesis of Homogeneous Artificial Proteins," *J. Am. Chem. Soc. 116*: 30-33, 1994.

Sahl and Bierbaum, "Lantibiotics: Biosynthesis and Biological Activities of Uniquely Modified Peptides from Gram-Positive Bacteria," *Annu. Rev. Microbiol. 52*: 41-79, 1998.

Senitzer and Freimer, "Autoimmune Mechanisms in the pathogenesis of Rheumatic Fever," *Reviews of Infectious diseases 6*(6): 832-839, Nov.-Dec. 1984.

Smith and Scott, "Libraries of Peptides and Proteins Displayed on Filamentous Phage," *Methods in Enzymology 217*: 228-257, 1993.

Stevens, D.L., "The Flesh-Eating Bacterium: What's Next?" *The Journal of Infectious Diseases 179*(Suppl. 2): S366-S374, 1999.

Tam, J.P., "Synthetic peptide vaccine design: Synthesis and properties of a high-density multiple antigenic peptide system," *Proc. Natl. Acad. Sci. USA 85*: 5409-5413, Aug. 1988.

Tam and Spetzler, "Chemoselective Approaches to the Preparation of Peptide Dendrimers and Branched Artificial Proteins Using Unprotected Peptides as Building Blocks," *Biomed. Pept. Proteins Nucleic Acids 1*(3): 123-132, 1995.

Theodore and Calandra, "Streptolysin S Activation by Lipoteichoic Acid," *Infection and Immunity 33*: 326-328, 1981.

Wannamaker, L. W., "Streptococcal Toxins," *Reviews of Infectious Diseases 5*(Suppl 4): S723-S732, Sep.-Oct. 1983.

\* cited by examiner

| | | AA | SEQ ID NO. |
|---|---|---|---|
| SLS prepropeptide | MLKFTSNILATSVAETTQVAPGGCCCCCTTCCFSIATGSGNSQGGSGSYTPGK | 53 | 2 |
| propeptide | CCCCCTTCCFSIATGSGNSQGGSGSYTPGK | 30 | 4 |
| synthetic peptide | FSIATGSGNSQGGSGSYTPGK | 21 | 6 |

Inhibition of β-Hemolysis by
S-SLS Antiserum

SEQUENCE LISTING

<160> NUMBER OF SEQ ID NOS: 8

<210> SEQ ID NO 1
<211> LENGTH: 159
<212> TYPE: DNA
<213> ORGANISM: Streptococcus pyogenes
<220> FEATURE:
<221> NAME/KEY: CDS
<222> LOCATION: (1)...(159)

<400> SEQUENCE: 1

```
atg tta aaa ttt act tca aat att tta gct act agt gta gct gaa aca      48
Met Leu Lys Phe Thr Ser Asn Ile Leu Ala Thr Ser Val Ala Glu Thr
 1               5                  10                  15 act caa gtt gct cct gga ggc tgc tgt tgc tgt act act tgt tgc          96
Thr Gln Val Ala Pro Gly Gly Cys Cys Cys Cys Thr Thr Cys Cys
                20                  25                  30 ttc tca att gct act gga agt ggt aat tct caa ggt ggt agc gga agt     144
Phe Ser Ile Ala Thr Gly Ser Gly Asn Ser Gln Gly Gly Ser Gly Ser
            35                  40                  45 tat acg cca ggt aaa                                                  159
Tyr Thr Pro Gly Lys
 50
```

<210> SEQ ID NO 2
<211> LENGTH: 53
<212> TYPE: PRT
<213> ORGANISM: Streptococcus pyogenes

<400> SEQUENCE: 2

```
Met Leu Lys Phe Thr Ser Asn Ile Leu Ala Thr Ser Val Ala Glu Thr
 1               5                  10                  15

Thr Gln Val Ala Pro Gly Gly Cys Cys Cys Cys Thr Thr Cys Cys
                20                  25                  30

Phe Ser Ile Ala Thr Gly Ser Gly Asn Ser Gln Gly Gly Ser Gly Ser
            35                  40                  45

Tyr Thr Pro Gly Lys
 50
```

<210> SEQ ID NO 3
<211> LENGTH: 90
<212> TYPE: DNA
<213> ORGANISM: Streptococcus pyogenes
<220> FEATURE:
<221> NAME/KEY: CDS
<222> LOCATION: (1)...(90)

<400> SEQUENCE: 3

```
tgc tgt tgc tgc tgt act act tgt tgc ttc tca att gct act gga agt     48
Cys Cys Cys Cys Cys Thr Thr Cys Cys Phe Ser Ile Ala Thr Gly Ser
 1               5                  10                  15 ggt aat tct caa ggt ggt agc gga agt tat acg cca ggt aaa              90
Gly Asn Ser Gln Gly Gly Ser Gly Ser Tyr Thr Pro Gly Lys
                20                  25                  30
```

<210> SEQ ID NO 4
<211> LENGTH: 30
<212> TYPE: PRT
<213> ORGANISM: Streptococcus pyogenes

<400> SEQUENCE: 4

Cys Cys Cys Cys Cys Thr Thr Cys Cys Phe Ser Ile Ala Thr Gly Ser

```
                   1               5              10              15
Gly Asn Ser Gln Gly Gly Ser Gly Ser Tyr Thr Pro Gly Lys
            20                  25              30

<210> SEQ ID NO 5
<211> LENGTH: 63
<212> TYPE: DNA
<213> ORGANISM: Streptococcus pyogenes
<220> FEATURE:
<221> NAME/KEY: CDS
<222> LOCATION: (1)...(63)

<400> SEQUENCE: 5 ttc tca att gct act gga agt ggt aat tct caa ggt ggt agc gga agt      48
Phe Ser Ile Ala Thr Gly Ser Gly Asn Ser Gln Gly Gly Ser Gly Ser
  1               5                  10                  15 tat acg cca ggt aaa                                                  63
Tyr Thr Pro Gly Lys
            20

<210> SEQ ID NO 6
<211> LENGTH: 21
<212> TYPE: PRT
<213> ORGANISM: Streptococcus pyogenes

<400> SEQUENCE: 6

Phe Ser Ile Ala Thr Gly Ser Gly Asn Ser Gln Gly Gly Ser Gly Ser
  1               5                  10                  15

Tyr Thr Pro Gly Lys
            20

<210> SEQ ID NO 7
<211> LENGTH: 8
<212> TYPE: PRT
<213> ORGANISM: Artificial Sequence
<220> FEATURE:
<223> OTHER INFORMATION: Tag amino acid sequence

<400> SEQUENCE: 7

Asp Tyr Lys Asp Asp Asp Asp Lys
  1               5

<210> SEQ ID NO 8
<211> LENGTH: 8
<212> TYPE: PRT
<213> ORGANISM: Artificial Sequence
<220> FEATURE:
<223> OTHER INFORMATION: Tag amino acid sequence

<400> SEQUENCE: 8

Asp Leu Tyr Asp Asp Asp Asp Lys
  1               5
```

STREPTOCOCCAL STREPTOLYSIN S VACCINES

CROSS-REFERENCE TO RELATED APPLICATION

This application is a continuation-in-part application of U.S. patent application Ser. No. 09/975,455, filed Oct. 10, 2001 now abandoned, which claims the benefit of U.S. Provisional Patent Application No. 60/239,432 filed Oct. 10, 2000. These applications are incorporated herein by reference in their entireties.

STATEMENT OF GOVERNMENT INTEREST

This invention was made with research funds from the Department of Veterans Affairs and the U.S. Public Health Service, National Institute of Allergy and Infectious Diseases under Grant No. AI-10085. The government may have certain rights in this invention.

TECHNICAL FIELD

The present invention relates generally to streptococcal antigens and their role in eliciting an immune response, and in particular, to streptolysin S polypeptides, peptides, or variants thereof and nucleic acids encoding these proteins, antibodies thereto, and methods of producing and using streptolysin S polypeptides, peptides, or variants thereof.

BACKGROUND OF THE INVENTION

Group A *streptococci* (GAS) cause a wide variety of clinical syndromes, ranging from uncomplicated infections of the pharynx and skin to life-threatening necrotizing fasciitis and streptococcal toxic shock syndrome (Stevens, *J Infect Dis* 179:S366, 1999). Protection against infection is largely mediated by antibodies against the surface M protein of the organisms. M protein is an alpha-helical, coiled-coil molecule that extends from the surface with its hypervariable amino-terminus exposed to the outside and the conserved carboxy-terminus buried in the cytoplasm. The amino-terminus contains type-specific epitopes that evoke bactericidal antibodies that correlate with protection against the homologous serotype. The emm gene is located in a regulon that is controlled by the upstream positive regulator Mga. Depending on the serotype, the regulon may contain one, two or three emm and emm-like genes. In serotypes containing only one emm gene, deletion or interruption of the emm gene results in an avirulent organism that can no longer resist phagocytosis. In serotypes that express several emm-like genes, each may partially contribute to resistance to phagocytosis, but among the many defined surface proteins of group A *streptococci*, only antibodies against the M protein have been shown to be opsonic.

GAS are also known to have, or are suspected of having, other virulence determinants, including two cytolytic toxins referred to as streptolysin S (SLS) and streptolysin O (SLO). SLO is a well-characterized, oxygen-labile molecule that lyses eukaryotic cells after binding to membrane cholesterol (Kehoe et al., *Infect Immun* 55:3228, 1987). SLO is immunogenic in humans and the anti-SLO titer is widely used as an indicator of recent streptococcal infection. Until recently, the characterization of SLS had eluded many investigators. This oxygen-stable toxin is responsible for the β-hemolysis surrounding colonies of GAS grown on blood agar plates (Alouf and Loridan, *Methods Enzymol* 165:59, 1988). In addition to red blood cells, SLS lyses a wide variety of eukaryotic cells, including myocardial cells, kidney cells, platelets, lymphocytes, and neutrophils (Hryniewicz and Pryjma, *Infect Immun* 16:730, 1977; Ofek et al., *Infect Immun* 6:459, 1972). Early studies showed that SLS was an unstable polypeptide with a molecular weight of about 2.8 kDa (Bernheimer, *J Bacteriol* 93:2024, 1967), which was bound to carrier molecules such as serum albumin, RNA core, or lipoteichoic acid (Theodore and Calandra, *Infect Immun* 33:326, 1981). On the basis of molecular weight, SLS has been described as the most potent bacterial hemolysin (Wannamaker, *Rev Infect Dis* 5:S723, 1983). Injection of rabbits with partially purified preparations of SLS resulted in rapid death preceded by intravascular hemolysis and changes in the electrocardiogram (Wannamaker, supra). Unlike SLO, SLS is non-immunogenic, which may be the result of the toxicity of SLS for lymphocytes or possibly because it is always bound to a carrier making potential epitopes cryptic.

Providing polypeptides from *streptococci* containing non-M protein antigens, especially those that have neutralizing, mucosal, or opsonic epitopes, would enhance therapeutic tools available to protect against a variety of streptococcal infections. Therefore, there is a need in the art for the discovery and characterization of non-M protein antigens that are effective for treating or preventing against such infections, especially antigens that elicit an immune response that is effective against multiple serotypes of group A *streptococci*.

SUMMARY OF THE INVENTION

The present invention provides the discovery of a novel streptolysin S (SLS) polypeptide, peptide, or variants thereof from *streptococcus* species, which have at least one epitope distinct from M protein and function as an immunogen to elicit antibodies that are effective against multiple serotypes of *streptococci*.

In one aspect, the invention provides an antibody specific for a peptide immunogen wherein the peptide immunogen comprises at least eight contiguous amino acids with at least 80% amino acid identity to SEQ ID NO:4 and comprises at least one streptolysin S epitope. In one embodiment, the antibody includes at least one neutralizing epitope. In another embodiment, the antibody is specific for a peptide immunogen that is recombinant or synthetic. In yet other embodiments, the antibodies may be polyclonal or monoclonal.

In another aspect, the invention provides an antibody specific for a peptide immunogen linked to at least one additional amino acid sequence, wherein the peptide immunogen comprises at least eight contiguous amino acids with at least 80% amino acid identity to SEQ ID NO:4 and comprises at least one streptolysin S epitope. In one embodiment, the at least one additional amino acid sequence comprises a carrier. In other embodiments, the carrier is selected from the group consisting of ovalbumin, KLH, tetanus toxoid, diphtheria toxoid, albumin, lysozyme, gelatin, gamma globulin, cholera toxin B subunit, *E. coli* labile toxin B subunit, and flagellin. In another embodiment, the at least one additional amino acid sequence comprises a second immunogen. In further embodiments, the second immunogen comprises an M protein of group A *streptococci*, wherein the M protein may be an amino terminal portion or a C repeat region. In another embodiment, at least one antibody is specific for a streptolysin S epitope and at least one antibody is specific for an M protein epitope. In still another embodiment, the at least one antibody specific for the streptolysin S epitope is a neutralizing antibody and the at least one antibody specific for the M protein epitope is a serotype specific opsonic antibody that is not tissue cross-reactive and/or at least one antibody is a mucosal antibody. In yet another embodiment, the invention provides any one of the above peptide immunogens wherein the at least one additional amino acid sequence is linked to the peptide immunogen recombinantly or chemically. In another embodiment, the recombinant linker is at least two amino acids encoded by a restriction enzyme recognition site.

In still another aspect, the invention provides a composition comprising a peptide immunogen for eliciting an immune response in a subject that includes a 21 amino acid peptide consisting essentially of SEQ ID NO:6. In still another aspect, the invention provides a composition for eliciting an immune response in a subject, comprising a peptide immunogen comprising at least eight contiguous amino acids with at least 80% identity to SEQ ID NOS:5 or 6 and a second immunogen comprising a hybrid multivalent M polypeptide. In yet another aspect, the invention provides a composition comprising a hybrid immunogen for eliciting an immune response in a subject that includes a peptide immunogen comprising at least eight contiguous amino acids with at least 80% identity to SEQ ID S:5 or 6 linked to a hybrid multivalent M polypeptide. In one embodiment, the hybrid immunogen may have the peptide immunogen and the multivalent M polypeptide linked recombinantly or chemically. In other embodiments, the aforementioned compositions wherein the peptide immunogen and the multivalent M polypeptide components are recombinant or synthetic. In, another embodiment, the aforementioned compositions for eliciting an immune response in a subject wherein the subject is a human or an animal. In still another embodiment, the aforementioned compositions further comprising an adjuvant, wherein the adjuvant may be alum or Freund's. In yet another embodiment, the aforementioned compositions of the present invention are sterile.

In yet another aspect, this invention provides a vaccinating agent for eliciting an immune response against *streptococci*, comprising a physiologically acceptable diluent and a peptide of at least eight contiguous amino acids consisting essentially of at least 80% amino acid identity to a portion of SEQ ID NO:4 and comprising at least one streptolysin S epitope. One embodiment includes the vaccinating agent further comprising an adjuvant, wherein the adjuvant may be alum or Freund's. In another embodiment, there is a vaccinating agent for treating or preventing a streptococcal infection in a subject comprising any of the aforementioned antibodies, wherein the subject may be human or animal.

In a further aspect, this invention provides a method for eliciting an immune response against *streptococci*, comprising administering to a subject any of the aforementioned peptide immunogens and compositions thereof. One embodiment includes any of the aforementioned peptide immunogens and compositions thereof further comprising an adjuvant, wherein the adjuvant may be alum or Freund's. In another embodiment, the invention provides the aforementioned methods wherein the peptide immunogens and compositions thereof are administered by a route selected from topical, oral, intranasal, intramuscular, subcutaneous, and parenteral. In still another embodiment, the aforementioned methods wherein the subject is a human or an animal.

In a related aspect, this invention provides a method for eliciting an immune response against *streptococci*, comprising administering to a subject any of the aforementioned vaccinating agents. In one embodiment, the aforementioned vaccinating agents may further comprise an adjuvant, wherein the adjuvant may be alum or Freund's. In another embodiment, the invention provides the aforementioned vaccinating agent administered by a route selected from topical, oral, intranasal, intramuscular, subcutaneous, and parenteral. In still another embodiment, the aforementioned methods of administering the aforementioned vaccinating agents wherein the subject is a human or an animal. In still another embodiment, the present invention provides a vaccinating agent for protecting an animal against a *streptococcus* infection comprising an antibody that specifically binds to an epitope present on the aforementioned SLS peptides. In another embodiment, the present invention provides methods for vaccinating a host against group A *streptococci* infections by administering the aforementioned vaccinating agents.

In another aspect, the present invention provides isolated nucleic acid molecules encoding the aforementioned SLS peptides as well as vectors containing the nucleic acid and host cell expressing the same. In one embodiment, provided is an isolated nucleic acid molecule comprising a sequence that encodes a peptide immunogen of at least eight contiguous amino acids with at least 80% amino acid identity to SEQ ID NOS:5 or 6 and comprising at least one streptolysin S epitope. In another embodiment, the aforementioned nucleic acid molecules wherein the encoded immunogen provides cross-protection against more than one serotype of group A *streptococci* when administered to a subject. In still another embodiment, the aforementioned nucleic acid molecules further comprise an additional nucleic acid molecule encoding at least one additional amino acid sequence fused to the nucleic acid molecule encoding the peptide immunogen. In yet another embodiment, the additional nucleic acid sequence encodes a second immunogen for protecting a subject against a streptococcal infection. In a related embodiment, the second immunogen is an M protein of group A *streptococci*, wherein the M protein may be an amino terminal portion or a C repeat region. In a further embodiment, the additional nucleic acid sequence encodes a carrier polypeptide. In a related embodiment, the carrier polypeptide is tetanus toxoid, diphtheria toxoid, albumin, lysozyme, gelatin, gamma globulin, cholera toxin B subunit, *E. coli* labile toxin B subunit, or flagellin. In yet another embodiment, the additional nucleic acid sequence encodes a tag amino acid sequence, wherein the tag is alkaline phosphatase, β-galactosidase, hexahistidine, FLAG® (DYKDDDDK, SEQ ID NO: 7), and GST.

In a related aspect, the present invention provides a nucleic acid expression construct comprising a promoter operably linked to any of the aforementioned isolated nucleic acid molecules. In another aspect, the invention provides a host cell containing the aforementioned nucleic acid expression constructs. In a related aspect, the invention provides a vaccinating agent for eliciting an immune response against *streptococci*, comprising a physiologically acceptable diluent and the aforementioned host cells. In yet another aspect, the present invention provides a method for producing a peptide immunogen, comprising growing any of the aforementioned host cells for a time sufficient to express the peptide immunogen encoded by the aforementioned nucleic acid expression constructs. In another aspect, this invention provides a peptide immunogen produced according to the aforementioned method for producing a peptide immunogen.

In another aspect, this invention provides a synthetic peptide immunogen for protecting a subject against a streptococcal infection, comprising a peptide or variants thereof of at least eight contiguous amino acids with at least 80% amino acid identity to a portion of SEQ ID NO:4. In one embodiment, the synthetic peptide immunogen elicits neutralizing antibodies specific for streptolysin S when administered to a subject. In another embodiment, the synthetic peptide immunogen elicits cross-protection against more than one serotype of group A *streptococci* when administered to a subject. In a further embodiment, the synthetic peptide immunogen is further linked to at least one additional amino acid sequence. In a related embodiment, the at least one additional linked amino acid sequence is a second immunogen for protecting a subject against a streptococcal infection. In another embodiment, the second immunogen comprises a portion of an M protein of group A *streptococci*, wherein the M protein may be an amino-terminal portion or a C repeat region. In still another embodiment, the M protein amino-terminal portion elicits serotype specific opsonic antibodies without eliciting tissue cross-reactive antibodies when administered to a subject. In another embodiment, the at least one additional amino acid sequence is a carrier polypeptide, wherein carrier polypeptide is ovalbumin, KLH, tetanus toxoid, diphtheria toxoid, bovine serum albumin, hen egg lysozyme, gelatin, bovine gamma globulin, cholera toxin B subunit, *E. coli* labile toxin B subunit, or flagellin. In other embodiments, the at least one additional amino acid sequence is linked recombinantly or chemically.

In another aspect, this invention provides composition for protecting a subject against a streptococcal infection, comprising a physiologically acceptable diluent and an effective amount of a an immunizing agent selected from (a) a peptide immunogen comprising an amino acid sequence with at least 80% amino acid identity to a portion of SEQ ID NO:4 and comprising at least one streptolysin S epitope; (b) an antibody specific for an epitope of a peptide of a); and (c) a host cell containing a nucleic acid expression construct comprising a promoter operably linked to an isolated nucleic acid molecule comprising a sequence that encodes a peptide immunogen of at least eight contiguous amino acids with at least 80% amino acid identity to SEQ ID NO:4 and comprising at least one streptolysin S epitope. In one embodiment, the immunizing agent is any of the aforementioned synthetic peptide immunogens. In another embodiment, the immunizing agent is linked to a carrier protein. In still another embodiment, the immunizing agent is the aforementioned peptide immunogen that is recombinantly or chemically linked to a carrier polypeptide. In another embodiment, the immunizing agent is any of the aforementioned host cells containing one of the aforementioned nucleic acid expression contructs. In another embodiment, the immunizing agent is any of the aforementioned antibodies.

In another aspect, this invention provides a method for protecting a subject against a *streptococcus* infection comprising administering to the subject any of the aforementioned compositions. One embodiment is a method of administering the aforementioned compositions that elicit neutralizing antibodies and/or mucosal antibodies and/or opsonic antibodies in a subject. In another embodiment, the aforementioned method provides protection against more than one serotype of *streptococci*. In still another embodiment, the aforementioned methods are applied wherein the route of administration is selected from topical, oral, intranasal, intramuscular, subcutaneous, and parenteral. In one other embodiment, the aforementioned method is administered to a human or an animal.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

Figures 1, 2:
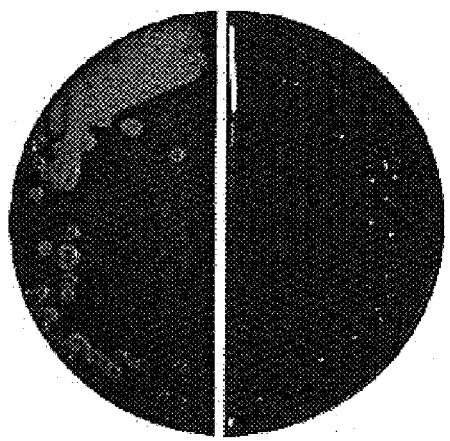
FIG. 1 shows the deduced amino acid sequence of the putative SLS prepropolypeptide (53 amino acids, which presumably includes a 23 amino acid leader sequence), putative SLS propolypeptide (30 amino acids) after predicted cleavage after GG amino acid pair, and a 21 amino acid truncated propolypeptide made for the present invention. All three SLS amino acid sequences were synthesized and none of the three SLS amino acid sequences showed any hemolytic activity (data not shown).
FIG. 2 shows the results of a blood agar plate assay that measures the level of SLS hemolytic activity inhibited by antibodies specific for SLS. Type 24 GAS were streaked on each side of the agar plate in the presence of preimmune serum (left side) and serum from a rabbit immunized with the 21 amino acid SLS peptide immunogen (SEQ ID NO:6) (right side).

As noted above, the present invention is generally directed to streptolysin S (SLS or SagA) polypeptides, peptides, and variants thereof, to isolated nucleic acids that encode such peptides, and to antibodies specific for such peptides. As used herein, "streptolysin S," "SLS," and "SagA" are used interchangeably and mean any polypeptide, peptide, or variant thereof, or nucleic acid encoding a polypeptide, peptide, or variant thereof having at least 50%, 60%, 70%, 80%, 90%, or 95% amino acid identity to the amino acid sequences provided herein as SEQ ID NOS:2, 4 or 6. As used herein, "percent identity" or "% identity" is the percentage value returned by comparing the whole of the subject polypeptide, peptide, or variant thereof sequence to a test sequence using a computer implemented algorithm, typically with default parameters. Sequence comparisons can be performed using any standard software program such as BLAST, tBLAST or MEGALIGN. Still others include those provided in the LASERGENE bioinformatics computing suite, which is produced by DNASTAR (Madison, Wis.). References for algorithms such as ALIGN or BLAST may be found in, for example, Altschul, *J. Mol. Biol.* 219:555–565, 1991; or Henikoff and Henikoff, *Proc. Natl. Acad. Sci. USA* 89:10915–10919, 1992. BLAST is available at the NCBI website. Other methods for comparing multiple nucleotide or amino acid sequences by determining optimal alignment are well known to those of skill in the art (see, e.g., Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," in Methods in Gene Biotechnology, pages 123–151 (CRC Press, Inc. 1997); and Bishop (ed.), Guide to Human Genome Computing, 2nd Edition, Academic Press, Inc., 1998).

The SLS polypeptides, peptides, or variants thereof of the present invention may be produced recombinantly or synthetically. One application of the disclosed invention is to prepare nucleic acid expression vectors for preparing SLS peptides. In certain aspects, the SLS peptides may be used as an immunogen to immunize a subject against streptococcal infections and further provide cross-protection against more than one serotype of *streptococci*. In another aspect, the present invention provides an antibody that is specific for an SLS peptide immunogen. Thus, a preferred method of immunizing a subject (e.g., humans or animals) against a streptococcal infection involves administering the polypeptides and compositions as described herein, such as an SLS peptide immunogen, an SLS peptide immunogen having a neutralizing epitope, an SLS peptide immunogen mixed with or fused with other streptococcal antigens (e.g., M protein or streptococcal protective antigen (Spa)), a host cell expressing an SLS peptide immunogen having an neutralizing epitope, or an antibody that is specific for an SLS peptide immunogen. Accordingly, the compositions and methods of the subject invention may be readily used to treat or prevent streptococcal infections.

I. Polypeptides, Peptides, and Variants Thereof

SLS is an oxygen-stable β-hemolysin produced by group A *streptococci* (GAS), which has been extensively studied and yet remains poorly understood. Although highly purified preparations of naturally produced SLS have not been successfully prepared, SLS is known to damage a variety of cellular membranes, including lymphocytes, neutrophils, platelets, tissue culture cells, tumor cells, lysosomes, and mitochondria (see Nizet et al., *Infect. Immun.* 68:4245, 2000, and references cited therein). However, SLS is considered to be non-immunogenic (Wannamaker, *Rev. Infect. Dis.* 5:S723, 1983; Betschel et al., *Infect. Immun.* 66:1671, 1998; Nizet et al., supra). The present invention provides various SLS polypeptides (e.g., SEQ ID NOS:2, 4, and 6).

By way of background and not wishing to be bound by theory, SEQ ID NO:1 is a nucleic acid sequence (referred to as the sagA gene; see also Betschel et al., supra) that is predicted to encode a full length, 53 amino acid polypeptide known as the SLS prepropolypeptide (SEQ ID NO:2). The SLS prepropolypeptide is subsequently cleaved by a leader peptidase, which presumably results in a 30 amino acid SLS propolypeptide (SEQ ID NO:4) and is ultimately subjected to post-translational modification when naturally produced by *streptococci*. As provided herein, a 21 amino acid SLS peptide immunogen (SEQ ID NO:6), which is a truncated version of the SLS propolypeptide useful for eliciting an immune response in a subject to protect against or treat a streptococcal infection. In one preferred embodiment, there is provided a peptide immunogen for eliciting an immune response in a subject, comprising a 21 amino acid peptide consisting essentially of SEQ ID NO:6. In a more preferred embodiment, these SLS peptide immunogens elicits neutralizing antibodies specific for streptolysin S when administered to a subject and preferably elicits cross-protection against more than one serotype of group A *streptococci* when administered to a subject.

A surprising result of the instant invention is that synthetic and recombinant SLS polypeptides, peptides, and variants thereof may be used to elicit antibodies specific for a SLS polypeptide, peptide and variants thereof, particularly in light of prior teachings. As noted above, injection of rabbits with partially purified preparations of naturally expressed SLS resulted in rapid death and no immune response. As described herein, the present invention provides SLS polypeptide, peptide, and variants thereof that can be used as an immunogen to elicit SLS-specific antibodies, including antibodies that neutralize the toxic activity of the naturally produced SLS toxin. In addition, a SLS peptide immunogen may be recombinantly or chemically combined with a carrier polypeptide. Alternatively, or in addition, a SLS peptide immunogen may be recombinantly or chemically combined, or merely mixed, with a second immunogen, including without limitation M protein amino-terminal portion or C repeat region, hybrid multivalent M protein, or Spa. Thus, a vaccinating agent may be used to elicit antibodies specific for SLS and other streptococcal antigens. For example, a vaccinating agent may include, inter alia, an SLS peptide immunogen that can elicit neutralizing antibodies specific for an SLS epitope, an M protein C repeat region that can elicit mucosal antibodies, and an M protein amino-terminal portion that can elicit opsonic antibodies that are not tissue cross-reactive.

As noted herein, the SLS polypeptides, peptides, and variants thereof may be produced synthetically or recombinantly; preferably a SLS peptide immunogen comprises at least eight contiguous amino acids with at least 80% identity to SEQ ID NOS:4 or 6 and comprises at least one streptolysin S epitope. As used herein, an "epitope" (i.e., antigenic determinant) is the site on an antigen, or antigenic portion of a peptide or polypeptide, at which an antibody can associate (i.e., can elicit the production of antibodies specific for a cell or particle having the antigen). A variety of techniques for mapping epitopes on a protein antigen are known in the art. Briefly, "classical" epitope mapping may be accomplished by using defined fragments of nucleic acid encoding a candidate SLS peptide immunogen that is expressed as a recombinant fusion protein and probed with SLS anti-sera in various assays, such as western blot or ELISA. Epitopes may also be mapped by using phage display technology wherein defined fragments of nucleic acid encoding a candidate SLS peptide immunogen are cloned into the phage protein pIII of the filamentous phage fuse-5 and are displayed on the surface of the phage, which recombinant phage can be captured with SLS anti-sera (see, e.g., Smith and Scott, *Methods Enzymol.* 217:228, 1993). Another known method for mapping epitopes is peptide scan technology wherein small overlapping oligopeptides (that ideally cover the complete SLS amino acid sequence, such as for SEQ ID NO:4) are synthesized on a solid support and probed with SLS anti-sera, which also allows rapid identification of SLS variants (see, e.g., U.S. Pat. Nos. 5,719,060 and 6,225,047.

Thus, preferred embodiments are SLS peptide immunogens that comprise at least eight contiguous amino acids with at least 80% identity to SEQ ID NO:4 and at least one SLS epitope, wherein the peptide immunogens should be understood to include immunogens of any integer within the range of SEQ ID NO:4 and does not include SLS prepropolypeptide (i.e., full length) defined by SEQ ID NO:2. For example, SLS peptide immunogens of the present invention may include peptides ranging in size from eight to 30 amino acids in length, which peptides may vary from SEQ ID NO:4 by about 20% as long as an SLS epitope remains in the variant. Preferably, a SLS peptide immunogen comprises 8, 9, 10, 11, 12, 13, 14, 15, 16, 17, 18, 19, 20, 21, 22, 23, 24, 25, 26, 27, 28, 29, or 30 amino acids of SEQ ID NO:4, and most preferably a 21 amino acid peptide. In a preferred embodiment, the sequence of a SLS peptide immunogen comprising at least one SLS epitope is linearly contiguous (i.e., sequence of amino acids that are identical to, or conservative variants of, a primary SLS amino acid sequence) or conformationally contiguous (i.e., amino acids brought together due to natural folding of the SLS polypeptide, peptide, or variant thereof) with that of the sequence for SLS, such that antibodies directed against the SLS peptide immunogen will also recognize a native SLS toxin molecule.

In one preferred embodiment, a synthetic peptide immunogen is provided for protecting a subject against a streptococcal infection, comprising a peptide or variants thereof of at least eight contiguous amino acids with at least 80% amino acid identity to a portion of SEQ ID NO:4. More preferably, the SLS peptide immunogen elicits neutralizing antibodies and cross-protection against more than one serotype of Sterptococci when administered to a subject. Even more preferably, the cross-protection is against any M protein serotype of group A streptococci. By way of background and as described herein, M proteins are a major surface protein and virulence factors for group A streptococci, with more than 100 distinct serotypes identified. As used herein, "M protein" means the M protein superfamily (see Cunningham, Clin. Micorbiol. Rev. 13:470, 2000), which includes immunoglobulin-binding proteins, M-related proteins (e.g., Spa), and M proteins. Furthermore, reference top a particular M serotype includes all related subtypes (e.g., M1 includes M1.1, M1.2, etc., and M13 includes M13W or M13L, etc.). Thus, cross protection may be against group A streptococci having, for example, serotypes 1, 2, 3, 4, 11, 12, 13, 14, 18, 19, 22, 24, 29, 33, 43, 48, 49, 52, 75, 89, 92 and 101.

The present invention also provides a SLS peptide immunogen, synthetic or recombinant, wherein the peptide immunogen is further linked to at least one additional amino acid sequence. In one preferred embodiment, the at least one additional amino acid sequence linked to a SLS peptide immunogen is a carrier polypeptide. Without wishing to be bound by theory, a synthetic SLS peptide chemically linked to keyhole limpet hemocyanin (KLH) may be used to elicit antibodies specific for an SLS epitope produced recombinantly or synthetically, which antibodies would alter (i.e., completely or partially inhibit) the hemolytic activity of the SLS toxin. For example, a synthetic SLS peptide including amino-acid residues 10–30 of the putative SLS propeptide (S-SLS(10–30)C, see Example 1) was made with a cysteine residue added at the carboxy-terminus (to facilitate conjugating a carrier). Then, S-SLS(10–30)C was linked to KLH and administered to a subject (i.e., a rabbit), which peptide acted as an immunogen and elicited antibodies capable of neutralizing the hemolytic activity of SLS in vitro or in vivo.

SLS peptide immunogens and additional amino acid sequences can be linked to form a hybrid immunogen or immunogen:carrier complex by a variety of methods, as provided herein and known in the art (see, generally, Jackson et al., Vaccine 18:355, 2000). Recombinant or synthetic peptides can be linked to form linear (see, e.g., Leclerc, et al., Eur. J Immunol. 17:26, 1987 and Francis, et al., Nature 330:168, 1987) or branched (see, e.g., Fitzmaurice, et al., Vaccine 14:553, 1996) constructs or using chemical ligation of epitopes (see, e.g., Tam and Spetzler, Biomed. Pept. Proteins Nucleic Acids 1:123, 1995; Rose, J. Am. Chem. Soc. 116:30, 1994; and Dawson, et al., Science 266:776, 1994). Peptides can also be linked via the multiple antigenic peptide system (see, e.g., Tam, Proc. Natl. Acad. Sci. USA 85:5409, 1988 and Tam, U.S. Pat. No. 5,229,490, issued Jul. 20, 1993). The multiple antigen peptide system makes use of multifunctional core molecules (e.g., lysines), where each of the functional groups on the core molecule forms at least two branches, the principal units of which are also multifunctional. Each multifunctional unit in a branch provides a base for added growth, resulting in exponential growth of the dendritic polymer. Peptides are then joined to the dendritic core using a linking molecule (e.g., glycine). The multiple antigen peptide system links a large number of synthetic peptides to the functional group of a dendritic core molecule providing a high concentration of synthetic peptides in a low molecular volume. The multiple antigen peptide system can include a lipophilic anchoring moiety attached to the core molecule, thereby eliminating the need for an adjuvant formulated in a peptide vaccine otherwise requiring one for immunostimulation (Tam, U.S. Pat. No. 5,580,563, issued Dec. 3, 1996). Additionally, similar or different synthetic peptides can be linked by controlled polymerization through derivatization of the amino-terminus of a peptide with the acryloyl ($CH_2$=CH—) group using acryloyl chloride (see, e.g., O'Brien-Simpson et al., J. Am. Chem. Soc. 119:1183, 1997 and Jackson et al., Vaccine 15:1697, 1997). The derivatized peptides are then polymerized singly or in admixture with similarly derivatized peptides by free radical initiation of chain elongation. As a result, peptides are assembled into polymers in which the peptide determinants form side chains pendant from an alkane backbone. The SLS peptide immunogens and fusion proteins may be constructed as set forth above.

Assays that detect in vitro hemolytic activity of streptococci or SLS toxin on blood, such as on an agar plate or in solution, are well known in the art and are described herein (see Examples 3 and 6). In a preferred embodiment, the SLS polypeptide, peptide, or variants thereof comprises at least one SLS epitope, which would be useful as an immunogen or as a vaccinating agent to treat, prevent, or inhibit infection or damage caused by streptococci. As described herein, the specificity of the antibodies to SLS may be detected by preincubating the immune serum containing antibody specific for SLS with soluble, unconjugated SLS peptide to inhibit the ability of the anti-SLS antibodies to alter hemolysis (see Example 5). In addition, antibodies from immune sera may be affinity purified, for example, using a S-SLS (10–30)C peptide column, which in the present invention yielded antibodies capable of completely inhibiting SLS-mediated hemolysis (see Examples 4 and 5).

By way of example, a combination of polyacrylamide gel electrophoresis, antibody binding and hemolytic activity assays may be used to separate and identify SLS polypeptides, peptides, or variants thereof comprising at least one neutralizing epitope. Briefly, a recombinantly or synthetically produced SLS peptide is separated by electrophoresis on a SDS polyacrylamide gel and then transferred onto nitrocellulose paper or other suitable solid surface. The nitrocellulose paper is contacted with immune sera prepared against the SLS peptide to absorb antibodies. The absorbed immune sera are then used in an opsonization assay. These results are compared to the results obtained with unabsorbed antisera. SLS polypeptides with neutralizing epitopes will absorb neutralizing antibodies from the test immune sera onto the nitrocellulose strips so that the residual immune sera will show reduced activity (inhibition) in a hemolysis activity assay in comparison to unabsorbed antisera. In one embodiment, a duplicate immunoblot is subjected to ordinary western blotting to confirm the presence of immunoreactive SLS polypeptides. Additionally, a duplicate polyacrylamide gel can be prepared to aid in purification of SLS polypeptides shown to contain neutralizing epitopes by the hemolysis activity assays.

In one embodiment, the SLS polypeptide, peptide, and variants thereof may be isolated and purified by any polypeptide purification techniques known in the art. As used herein, "isolated" refers to material that has been separated from its original environment (e.g., the natural environment if it is naturally occurring). For example, a naturally occurring nucleic acid or polypeptide present in a living animal is not isolated, but the same nucleic acid or polypeptide is isolated when separated from some or all of the co-existing materials in the natural system such as carbohydrate, lipid, or other proteinaceous impurities associated with the molecule in nature. Nucleic acids or polypeptides may be part of a composition and still be isolated in that such fragment, vector, or composition is not part of its natural environment. Within certain embodiments, a particular protein preparation contains an "isolated polypeptide" if it appears nominally as a single band on SDS-PAGE gel with Coomassie Blue staining. In certain other embodiments, an isolated polypeptide or peptide molecule is a chemically synthesized polypeptide or peptide molecule. Further, to "purify" means to isolate a fraction wherein the desired species represents 50%–100% of all extracted polypeptides present in the fraction. For further characterization of recombinant SLS peptides, it is preferred that the SLS peptide comprise at least 90% and more preferably at least 95% of the polypeptides in the purified fraction. Typical isolation steps useful in the practice of this invention include, but are not limited to, ammonium sulfate precipitation, polyacrylamide gel electrophoresis and HPLC. These techniques are suitable to provide an isolated SLS peptide or fusion protein (as described below) of sufficient quantity and purity to obtain an amino-terminal sequence and to raise specific antibodies in an animal, such as a rabbit.

An in vivo method for assessing SLS toxin activity or streptococcal virulence is, for example, by an intraperitoneal challenge infection in an animal immunized with a SLS peptide immunogen of the present invention. Briefly, this method determines the dose of bacterial particles necessary to be lethal in a test animal, usually a mouse. Virulence is scored by calculating the number of bacteria that are lethal to 50% of the test animals after intraperitoneal injection ($LD_{50}$). Typically, a virulent strain will have an $LD_{50}$ of less than $10^6$ in a mouse. For example, a type 18 group A *streptococcus* parent strain has an $LD_{50}$ of $0.73 \times 10^5$; therefore, the efficacy of peptide immunogen for protecting an animal against a *streptococcus* infection may be measured, for example, by challenging a mouse pre-immunized with an SLS peptide immunogen of the present invention to determine whether the $LD_{50}$ increases (i.e., provides protection). The present invention demonstrates for the first time that it is possible to elicit antibodies, and preferably neutralizing antibodies, against SLS, which is one of the most potent bacterial cytolytic toxins known. As described herein, the synthetic or recombinant SLS peptide immunogen may be used as an important component of vaccines designed to prevent GAS infections.

The dermonecrotic mouse model is another in vivo method for assessing the ability of antibodies specific for SLS peptide immunogens to alter SLS activity (i.e., a model for invasive streptococcal infections). Briefly, streptococcal cultures may be grown to mid-log phase, contacted with preimmune rabbit serum and anti-SLS immune rabbit serum, then injected subcutaneously into a mouse, and necrotic lesions are assessed. The *streptococci* contacted with the preimmune serum should produce necrotic lesions whereas the *streptococci* contacted with the immune serum should show reduced or no necrotic lesions. In one preferred embodiment, provided is a composition for protecting a subject against a streptococcal infection, comprising a physiologically acceptable diluent and an effective amount of a an immunizing agent, wherein the immunizing agent is a peptide immunogen comprising an amino acid sequence with at least 80% amino acid identity to a portion of SEQ ID NO:4 and comprising at least one streptolysin S epitope.

Vaccinating agents of the present invention may be synthesized chemically (see, e.g., Beachey et al., *Nature* 292: 457–459, 1981), or generated recombinantly. As used herein, a "vaccinating agent" is a composition capable of eliciting a protective immune after the vaccinating agent is administered to a subject. The vaccinating agent may be either protein- or DNA-based (e.g., a gene delivery vehicle). Within further aspects, a cell may be generated to be a vaccinating agent, and designed to express an immunogenic polypeptide or multivalent construct of the present invention. For recombinant production, PCR primers may be synthesized to amplify desired 3' sequences of sagA and, for example, where hybrid or fusion polypeptides are involved, the 5' sequences of each emm or spa gene may be used. Each primer is designed to contain a unique restriction enzyme recognition site that is subsequently used to ligate the individual PCR products either individually or in tandem into a suitable vector or nucleic acid expression construct. In one preferred embodiment, the restriction enzyme recognition site will encode at least a two amino acid linker.

In other preferred embodiments, a second immunogen from, for example, *streptococci* or unrelated pathogens may be combined with a SLS peptide immunogen, as disclosed herein, into a single fusion protein, which may function either as an immunogen or as a carrier polypeptide. Alternatively, the SLS peptide immunogens of the present invention may be further chemically (rather than recombinantly) linked to a second amino acid sequence, wherein the second amino acid sequence is a carrier polypeptide. Second immunogens against some pathogens might include T and B cell epitopes originally derived from different proteins and included as a hybrid construct with an SLS peptide immunogen. Also, multivalent hybrid proteins with SLS peptides may be sufficient conjugates in carbohydrate vaccines, such as those for *Streptococcus pneumoniae, Haemophilus influenzae* B or group B *streptococci*. Preferably, there is a composition for eliciting an immune response in a subject, comprising a peptide immunogen comprising at least eight contiguous amino acids with at least 80% identity to SEQ ID NOS:4 or 6 and a second immunogen comprising a hybrid multivalent M polypeptide. In another preferred embodiment, the composition includes a hybrid immunogen for eliciting an immune response in a subject that comprises a peptide immunogen of at least eight contiguous amino acids with at least 80% identity to SEQ ID NOS:4 or 6 linked to a hybrid multivalent M polypeptide. In this regard, a preferred vaccinating agent includes fusion proteins developed from a combination of SLS peptides of SEQ ID NOS:4, or 6 with a second amino acid sequence, such as an amino-terminal M protein portion, a M protein C repeat, or a hybrid multivalent polypeptide (see, e.g., U.S. Pat. No. 6,063,386). For example, without limitation, representative examples may include fusion polypeptides such as 24-5-SLS-6-19; 24-SLS-5-6-19-1-3; or 1-3-5-SLS-6-18-19-24-Spa-30. A person having ordinary skill in the art will appreciate that the position of a SLS peptide among other peptides in a multivalent fusion polypeptide may be varied, preferably placed at an internal position and preferably not at the carboxy-terminal position of the fusion polypeptide. Alternatively, for example, there may be a cocktail mixture of hybrid multivalent M protein, such as 19-24-5-6-19-1-3 or 1-3-5-Spa-6-18-19-24, and a SLS peptide immunogen of at least eight contiguous amino acids with at least 80% identity to SEQ ID NO:4.

The amino-terminal M protein portion and C repeat region of M protein are capable of eliciting opsonic antibodies and mucosal antibodies, respectively (see Cunningham, supra). In one embodiment, the epitope is "opsonic," which as used herein means any epitope that enhances phagocytosis of a cell or particle having the epitope. As commonly understood by those having ordinary skill in the art, "opsonic antibodies" are antibodies that facilitate phagocytic activity of a particle having the antigen, such as a bacterial cell. In a preferred embodiment, the epitope is "neutralizing," which as used herein means an epitope defined by an antibody that is specific for that epitope and the binding of the antibody to the epitope alters the activity of an enzyme (such as streptococcal proteinase or C5a peptidase) or a toxin (such as SLS or SLO). As used herein, "mucosal" antibody means antibodies, such as IgA, elicited by natural infection or induced by immunization at rectal, genital and oral mucosal surfaces.

Another exemplary in vitro assay is an opsonophagocytosis assay, which detects phagocytosis facilitated by the presence of opsonic antibodies present in test antisera. Briefly, the assay measures the amount of phagocytosis of selected bacterial particles by neutrophils after preincubating the particles in the presence or absence of antisera raised against, for example, SLS peptide immunogens combined with amino-terminal M protein protions that have at least one opsonic epitope. Preincubation with the immune sera coats the particles with M protein reactive antibodies, some of which will be opsonic antibodies elicited from opsonic epitopes present on the M protein antigens. Preincubated, coated particles are then mixed with whole blood from an animal, typically a mammal for which opsonic protection is to be sought (e.g., a human) to determine the percentage of neutrophils that associate with the bacterial particles, which is a measure of phagocytic activity facilitated by opsonic antibodies. Immune sera containing opsonic antibodies induce a higher percentage of neutrophils associated with the selected bacteria than does immune sera lacking opsonic antibodies. In a variation of this test, the bactericidal activity of immune sera may be tested by incubating the immune sera with fewer bacterial particles, incubating in blood for a longer period of time, and then plating the mixture on a culture medium to score for viable bacteria. The presence of opsonic antibodies in the immune sera increase the number of bacteria destroyed by phagocytosis and, therefore, lowers the number of colony forming units (CFUs) detected on the plate culture.

As noted above, the invention provides SLS fusion polypeptides encoded by nucleic acids that have a SLS polypeptide, peptide, or variant thereof coding sequence fused in frame to an additional amino acid coding sequence to provide for expression of an SLS protein sequence fused to an additional functional or non-functional polypeptide sequence that permits, for example by way of illustration and not limitation, detection, isolation and/or purification of the SLS fusion polypeptide. Such SLS fusion polypeptides may permit detection, isolation and/or purification of the SLS fusion polypeptide by protein-protein affinity, metal affinity or charge affinity-based polypeptide purification, or by specific protease cleavage of a fusion polypeptide containing a fusion sequence that is cleavable by a protease such that the SLS polypeptide, peptide, or variant thereof is separable from the second polypeptide, peptide, or variant thereof. In a preferred embodiment, the SLS peptide immunogen is linked to a tag amino acid sequence, such as alkaline phosphatase, β-galactosidase, hexahistidine, the FLAG® epitope tag (DYKDDDDK, SEQ ID NO: 7; see e.g., U.S. Pat. No. 5,011,912 and Hopp et al., *Bio/Technology* 6:1204, 1988), the XPRESS™ epitope tag (DLYDDDDK, SEQ ID NO: 8; Invitrogen, Carlsbad, Calif.), the myc epitope tag (e.g., Roche Molecular Biochemicals, Indianapolis, Ind.), and GST.

II. Nucslic Acids

The invention also encompasses isolated nucleic acid molecules comprising a sequence that encodes a *streptococcus* SLS polypeptide, peptide, or variant thereof (e.g., SEQ ID NOS:1, 3, and 5). Also provided by the present invention are nucleic acid expression constructs, and host cells containing such nucleic acids, which encode SLS polypeptides, peptides, and variants thereof, which have at least one SLS epitope. This aspect of the invention pertains to isolated nucleic sequences encoding a SLS sequence as described herein, as well as those sequences readily derived from isolated nucleic molecules such as, for example, complementary sequences, reverse sequences and complements of reverse of sequences.

"Nucleic acid" or "nucleic acid molecule" refers to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids may be composed of monomers that are naturally-occurring nucleotides (such as deoxyribonucleotides and ribonucleotides), analogs of naturally-occurring nucleotides (e.g., α-enantiomeric forms of naturally-occurring nucleotides), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety may be replaced with sterically and electronically similar structures, such as azasugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids," which comprise naturally-occurring or modified nucleic acid bases attached to a polyamide backbone. Nucleic acids can be either single stranded or double stranded.

Further, an "isolated nucleic acid molecule" refers to a polynucleotide molecule in the form of a separate fragment or as a component of a larger nucleic acid construct, which has been separated from its source cell (including the chromosome it normally resides in) at least once in a substantially pure form. For example, a DNA molecule that encodes a SLS polypeptide, peptide, or variant thereof, which has been separated from a *Streptococcus* cell or from the genomic DNA of a *Streptococcus* cell, is an isolated DNA molecule. Another example of an isolated nucleic acid molecule is a chemically synthesized nucleic acid molecule. Nucleic acid molecules may be comprised of a wide variety of nucleotides, including DNA, cDNA, RNA, nucleotide analogues, or some combination thereof.

In one embodiment, isolated nucleic acid molecule comprising a sequence that encodes a peptide immunogen comprising at least eight contiguous amino acids with at least 80% amino acid identity to SEQ ID NOS:4 or 6 and at least one streptolysin S epitope. Variants of the SLS nucleic acid sequences include those selected from sequences that encode the polypeptides of SEQ. ID NOS: 2, 4 or 6, which are degenerate to SEQ. ID NOS: 1, 3 or 5 because of the genetic code; sequences that encode a polypeptide which has conservative amino acid substitutions to the polypeptide of SEQ ID NOS: 2, 4, or 6, or sequence that encode a polypeptide that is at least 80% identical to SEQ ID NO: 4 or 6. In still another embodiment, the invention provides an isolated nucleic acid molecule comprising a sequence that hybridizes to the aforementioned nucleic acid molecules under conditions of moderate or high stringency. Another embodiment includes isolated nucleic acid molecules comprising a sequence wherein the encoded immunogen comprises a neutralizing epitope and/or provides cross-protection against more than one serotype of group A *streptococci* when administered to a subject. Other related aspects of the nucleic acid sequences provided herein include SLS nucleic acid molecules further comprising an additional nucleic acid molecule fused to the nucleic acid molecule encoding the peptide immunogen, wherein the additional nucleic acid molecule encodes at least one additional amino acid sequence. In one embodiment, the additional nucleic acid sequence encodes a second immunogen for protecting a subject against a streptococcal infection, such as an M protein of group A *streptococci*. Preferably, the M protein of group A *streptococci* is an amino-terminal portion or a C-repeat region. In another embodiment, the additional nucleic acid sequence encodes a carrier, such as tetanus toxoid, diphtheria toxoid, albumin, lysozyme, gelatin, gamma globulin, cholera toxin B subunit, *E. coli* labile toxin B subunit, and flagellin. In yet another preferred embodiment, the additional nucleic acid sequence encodes a tag amino acid sequence, such as alkaline phosphatase, β-galactosidase, hexahistidine, FLAG® (DYKDDDDK, SEQ ID NO: 7) and GST.

A related embodiment to the aforementioned isolated nucleic acid molecules includes a nucleic acid expression construct comprising a promoter operably linked to the isolated nucleic acid molecule such that a SLS polypeptide or fusion protein as described herein is expressed in a host cell. In another embodiment, the invention provides a host cell containing such a nucleic acid expression construct. In a related embodiment, the invention provides a method for producing a peptide immunogen, comprising growing the described host cells for a time sufficient to express the peptide immunogen encoded by the nucleic acid expression construct.

As used herein, a sagA gene is a *streptococcus* gene or nucleic acid variant thereof. For example, an isolated nucleic acid that encodes at least 8 amino acids of a SLS polypeptide of SEQ. ID NOS:6; an isolated nucleic acid that encodes a SLS propolypeptide or peptide such as SEQ. ID NOS:4; and an isolated nucleic acid that encodes a native SLS prepropolypeptide, such as SEQ. ID NOS:2. One example of part of a sagA gene is set forth in SEQ ID NOS:1, 3, and 5. As is known in the art, the 53 amino acid sequence represents full-length SagA.

Another aspect of the isolated sagA nucleic acids of this invention includes fragments of isolated sequences. As used herein, a "fragment" of an isolated sagA gene includes any nucleic acid sequence comprising at least 12 nucleotides from an isolated sagA gene or a variant of least 12 nucleotides that hybridizes to an isolated sagA gene under conditions of moderate or high stringency. Such sequences are useful for a variety of purposes, including PCR primers for isolating additional sagA sequences or variants thereof from other *streptococci*. Another typical use is for recombinant expression of a peptide or polypeptide comprised of epitopes present on a native SLS polypeptide.

Also provided herein are nucleic acid fragments or oligonucleotides useful as probes and/or primers for identifying or obtaining SLS sequences. More specifically, a nucleic acid fragment or oligonucleotide that comprise at least 12 contiguous nucleotides of SEQ ID NO:1, 3 or 5 are particularly useful as probes for hybridization to SLS nucleic acid sequences and/or as primers for amplification of the same. More particular embodiments include nucleic acid fragments or oligonucleotides where the length is at least 18, 24, 30, 50 or greater than 50 nucleotides, or a length of any integer within the range of 12 to about 100 nucleotides. Complementary nucleic acid sequences of the above sequences are also included.

Another embodiment of nucleic acid fragments or oligonucleotides of this invention include those that encode a SLS peptide immunogen epitope that can be detected, for example, by the ability to specifically bind to an anti-SLS antibody or which can be used to elicit an immune response in a subject, such as a human or an animal. Useful peptide epitopes are those capable of eliciting antibodies specific for the SLS peptide or polypeptide, or that are capable of eliciting a T-cell response to the same. Peptide sequences of eight or more amino acids are useful in this regard because it is generally understood by those skilled in the art that eight amino acids is the lower size limit for a peptide to interact with the major histocompatibility complex (MHC). More preferred embodiments include nucleic acid fragments or oligonucleotides encoding at least 8, 10, 12, 15, 18, 21, 25, or 30 amino acids, or a sequence length of any integer in that range.

Accordingly, the present invention provides nucleic acid fragments or oligonucleotides encoding a peptide comprised of at least eight contiguous amino acids of the SLS sequence according to SEQ ID NOS:4, or 6. Particular embodiments of this aspect include nucleic acid fragments or oligonucleotides encoding a SLS peptide comprised of at least 8, 10, 12, 15, 18, 21, or 30 amino acids. Preferred embodiments include nucleic acid fragments wherein the encoded peptide comprise sequences from a SLS polypeptide that maintains 80% amino acid identity, and more particularly, sequences comprising at least one neutralizing epitope. These include, for example, sequences encoding peptides contained within SEQ ID NOS:4 or 6, as described herein.

The invention also provides nucleic acid molecules useful for modulating or inhibiting the expression of a sagA gene in a cell. More specifically, the invention provides for ribozymes that cleaves RNA encoding the aforementioned SLS polypeptides and for antisense molecules that bind to such an RNA. This includes nucleic acid molecules comprising a sequence that encodes such a ribozyme or antisense molecule and vectors comprising the same. Particular embodiments include vectors wherein the aforementioned ribozyme or antisense nucleic acid is operably linked to a promoter. Typical embodiments of these vectors are selected from the group consisting of plasmid vectors, phage vectors, herpes simplex viral vectors, adenoviral vectors, adenovirus-associated viral vectors and retroviral vectors. Host cells comprising the above vectors are also included.

"Vector" refers to an assembly that is capable of directing the expression of a desired polypeptide. The vector may include transcriptional promoter/enhancer elements that are operably linked to the gene(s) or isolated nucleic acid molecule(s) of interest. The vector may be composed of DNA", RNA, or a combination of the two (e.g., a DNA-RNA chimera). Optionally, the vector may include a polyadenylation sequence, one or more restriction sites, as well as one or more selectable markers, such as neomycin phosphotransferase or hygromycin phosphotransferase. Additionally, depending on the host cell chosen and the vector employed, other genetic elements such as an origin of replication, additional nucleic acid restriction sites, enhancers, sequences conferring inducibility or repressibility of transcription, and selectable markers, may also be incorporated into the vectors described herein.

"Cloning vector" refers to nucleic acid molecules, such as a plasmid, cosmid, or bacteriophage, which are capable of replicating autonomously in a host cell. Cloning vectors typically contain one or a small number of restriction endonuclease recognition sites, at which foreign nucleotide sequences can be inserted in a determinable fashion without loss of an essential biological function of the vector. Cloning vectors also typically containa marker gene that is suitable for use in the identification and selection of cells transformed with the cloning vector. Marker genes typically encode proteins that provide resistance to antibiotics, such as tetracycline, kanamycin, ampicillin, and the like.

As used herein, "nucleic acid expression construct" refers to a nucleic acid molecule construct encoding a gene that is expressed in a host cell. Typically, gene expression is placed under the control of a promoter, and optionally, under the control of at least one regulatory element. Such a gene is said to be "operably linked to" the promoter. Similarly, a regulatory element and a promoter are operably linked if the regulatory element alters (i.e., increases or decreases) the activity of the promoter. In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

As used herein, "promoter" refers to a nucleotide sequence that directs the transcription of a structural gene. Typically, a promoter is located in the 5' region of a gene, proximal to the transcriptional start site of a structural gene. If a promoter is an inducible promoter, then the rate of transcription may, for example, be increased by the addition of an inducing agent or decreased by the addition of an inhibiting agent. In contrast, an inducing or an inhibiting agent does not affect the rate of transcription of a constitutive promoter. A person having ordinary skill in the art is capable of selecting a suitable promoter and suitable host for expressing, for example, an isolated nucleic acid sequence encoding a peptide having the amino acid sequence of SEQ ID NO:4 or variants thereof, wherein the variants comprise amino acid sequences having conservative amino acid substitutions or having at least 80% sequence identity to SEQ ID NO:4.

As used herein, "host" refers to any prokaryotic or eukaryotic cell that contains either a cloning vector or nucleic acid expression construct. This term also includes those prokaryotic or eukaryotic cells that have been genetically engineered to contain the cloned gene(s) in the chromosome or genome of the host cell.

Ribozymes are provided which are capable of inhibiting expression of SLS RNA. As used herein, "ribozymes" are intended to include RNA molecules that contain anti-sense sequences for specific recognition, and an RNA-cleaving enzymatic activity. The catalytic strand cleaves a specific site in a target RNA at greater than stoichiometric concentration. A wide variety of ribozymes may be utilized within the context of the present invention, including for example, the hammerhead ribozyme (for example, as described by Forster and Symons, *Cell* 48:211–220, 1987; Haseloff and Gerlach, *Nature* 328:596–600, 1988; Walbot and Bruening, *Nature* 334:196, 1988; Haseloff and Gerlach, *Nature* 334: 585, 1988); the hairpin ribozyme (for example, as described by Haseloff et al., U.S. Pat. No. 5,254,678, issued Oct. 19, 1993 and Hempel et al., European Patent Publication No. 0 360 257, published Mar. 26, 1990); and Tetrahymena ribosomal RNA-based ribozymes (see Cech et al., U.S. Pat. No. 4,987,071). Ribozymes of the present invention typically consist of RNA, but may also be composed of DNA, nucleic acid analogs (e.g., phosphorothioates), or chimerics thereof (e.g., DNA/RNA).

Antisense oligonucleotide molecules are provided which specifically inhibit expression of Spa nucleic acid sequences (see, generally, Hirashima et al. in *Molecular Biology of RNA:New Perspectives* (M. Inouye and B. S. Dudock, eds., 1987 Academic Press, San Diego, p. 401); *Oligonucleotides: Antisense Inhibitors of Gene Expression* (J. S. Cohen, ed., 1989 MacMillan Press, London); Stein and Cheng, *Science* 261:1004–1012, 1993; WO 95/10607; U.S. Pat. No. 5,359, 051; WO 92/06693; and EP-A2-612844). Briefly, such molecules are constructed such that they are complementary to, and able to form Watson-Crick base pairs with, a region of transcribed SLS mRNA sequence. The resultant double-stranded nucleic acid interferes with subsequent processing of the mRNA, thereby preventing protein synthesis.

Within a related aspect, any of the aforementioned nucleic acids may include modified nucleotides. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids," which comprise naturally-occurring or modified nucleic acid bases attached to a polyamide backbone. Nucleic acids can be either single stranded or double stranded.

It should be understood that sagA genes include nucleic acid sequences encoding wild-type/native SLS polypeptides as well as other variants (including alleles). Briefly, such "variants" may result from natural polymorphisms or may be synthesized by recombinant methodology or chemical synthesis, and differ from wild-type polypeptides by one or more amino acid substitutions, insertions, deletions, or the like. Variants encompassing conservative amino acid substitutions include, for example, substitutions of one aliphatic amino acid for another, such as Ile, Val, Leu, or Ala or substitutions of one polar residue for another, such as between Lys and Arg, Glu and Asp, or Gln and Asn. Such substitutions are well known in the art to provide variants having similar physical properties and functional activities, such as for example, the ability to elicit and cross react with similar antibodies. Other variants include nucleic acids sequences that encode a polypeptide having at least 50%, 60%, 70%, 80%, 90% or 95% amino acid identity to SEQ ID NOS:4 or 6. Preferred embodiments are those having greater than 90% or 95% identity with the amino acid sequence of SEQ ID NOS:4 or 6. As will be appreciated by those of ordinary skill in the art, a nucleotide sequence encoding an SLS polypeptide, peptide, or variant thereof may differ from the native sequences presented herein due to codon degeneracy, nucleotide polymorphism, or nucleotide substitution, deletion or insertion. Thus, in certain aspects the present invention includes all degenerate nucleic acid molecules that encode polypeptides and peptides comprising the amino acid sequence of SEQ ID NOS:2 or 4 or 6. In another aspect, included are nucleic acid molecules that encode SLS variants having conservative amino acid substitutions or deletions or substitutions such that the SLS variant retains its hemolytic activity and/or retains epitopes capable of eliciting antibodies specific for SLS polypeptides, peptides, or variants thereof.

While particular embodiments of isolated nucleic acids encoding SLS polypeptides and peptides are depicted in SEQ ID NOS:1, 3, and 5, within the context of the present invention, reference to one or more isolated nucleic acids includes variants of these sequences that are substantially similar in that they encode native or non-native proteins, polypeptides or peptides with similar structure and function to the SLS polypeptide of SEQ. ID NOS:4 or 6. As used herein, the nucleotide sequence is deemed to be "substantially similar" if: (a) the nucleotide sequence is derived from the coding region of a sagA gene isolated from a *streptococcus* (including, for example, portions of the sequence or allelic variations of the sequences discussed above) and contains a non-M protein epitope with substantially the same ability to elicit opsonic antibodies protective against *streptococci* that are not tissue cross reactive; (b) the nucleotide sequence is capable of hybridization to the nucleotide sequences of the present invention under moderate or high stringency; (c) the nucleotide sequences are degenerate (i.e., sequences which code for the same amino acids using a different codon sequences) as a result of the genetic code to the nucleotide sequences defined in (a) or (b); or (d) is a complement of any of the sequences described in (a), (b) or (c).

"Moderate or stringent hybridization conditions" are conditions of hybridization of a probe nucleotide sequence to a target nucleotide sequence wherein hybridization will only be readily detectable when a portion of the target sequence is substantially similar to the complement of the probe sequence. Hybridization conditions vary with probe size as well as with temperature, time and salt concentration in a manner known to those of ordinary skill in the art. For example, moderate hybridization conditions for a 50 nucleotide probe would include hybridization overnight a buffer containing 5×SSPE (1×SSPE=180 mM sodium chloride, 10 mM sodium phosphate, 1 mM EDTA (pH 7.7), 5× Denhardt's solution (100× Denhardt=2% (w/v) bovine serum albumin, 2% (w/v) Ficoll, 2% (w/v) polyvinylpyrrolidone) and 0.5% SDS incubated overnight at 55–600° C. Post-hybridization washes at moderate stringency are typically performed in 0.5×SSC (1×SSC=150 mM sodium chloride, 15 mM trisodium citrate) or in 0.5×SSPE at 55–600° C. Stringent hybridization conditions typically would include 2×SSPE overnight at 420° C., in the presence of 50% formamide followed by one or more washes in 0.1–0.2×SSC and 0.1% SDS at 650° C. for 30 minutes or more.

Another aspect of the present invention is the use of isolated sagA nucleotide sequences to produce recombinant SLS proteins for immunizing an animal. One preferred embodiment is producing a SLS peptide immunogen using a host cell containing a nucleic acid construct to express such a product. The use of any length of nucleic acid disclosed by the present invention (preferably 24 nucleotides or longer) that encodes a polypeptide or variant thereof of at least eight contiguous amino acids, which is capable of binding to the major histocompatibility complex and eliciting or enhancing an immunogenic response is contemplated by this invention. Preferred embodiments include SLS peptides or variants thereof that elicit neutralizing antibodies. Immunogenic response can be readily tested by known methods such as challenging a mouse or rabbit with polypeptides or fragments of interest and thereafter collecting antisera and determining if the antibody of interest is present. Other assays particularly useful for the detection of T-cell responses include proliferation assays, T-cell cytotoxicity assays, assays for delayed hypersensitivity, and assays for opsonization, such as previously described. In determining whether an antibody specific for an antigen of interest is produced by the animal, many diagnostic tools are available, including, for example, testing binding of antigen to antibodies contained in a sample antisera using conventional western blotting, using enzyme-linked immunoassays with a tag attached to the antigen of interest, or inhibiting the function of the antibodies by exposure to the SLS peptides used to raise the antibodies.

The isolated nucleic acids encoding SLS polypeptides according to this invention can be obtained using a variety of methods. For example, a nucleic acid molecule may be obtained from a cDNA or genomic expression library by screening with an antibody or antibodies reactive with a SLS polypeptide (see, e.g., Sambrook et al., *Molecular Cloning: A Laboratory Manual,* Cold Spring Harbor, 1989; Ausubel et al., *Current Protocols in Molecular Biology,* Greene Publishing, 1987). Further, random-primed PCR can be employed (see, e.g., *Methods in Enzymol.* 254:275, 1995). In addition, variations of random-primed PCR can also be used, especially when a particular gene or gene family is desired. In one such method, one of the primers is a random primer and the other is a degenerate primer based on the amino acid sequence or nucleotide sequence encoding a Spa polypeptide.

Other methods may also be used to obtain isolated nucleic acid molecules that encode a SLS polypeptide. For example, a nucleic acid molecule can be isolated by using the sequence information provided herein to synthesize a probe which can be labeled, such as with a radioactive label, enzymatic label, protein label, fluorescent label, or the like, and hybridized to a genomic library or a cDNA library constructed in a phage, plasmid, phagemid, or viral vectors designed for replication or expression in selected host cells (see, e.g., Sambrook et al., supra; Ausubel et al., supra). DNA representing RNA or genomic nucleic acid sequence can also be obtained by amplification using sets of primers complementary to 5' and 3' sequences of the isolated nucleic acid sequences provided in SEQ ID NO:1 or to variants thereof as described above. For ease of cloning, restriction enzyme sites can also be incorporated into the primers.

Variants (including alleles) of the isolated sagA nucleic acid sequence provided herein can be readily obtained from natural variants (e.g., polymorphisms, mutants and other serotypes) either synthesized or constructed. Many methods have been developed for generating mutants (see, generally, Sambrook et al., supra; Ausubel et al., supra). Briefly, preferred methods for generating nucleotide substitutions utilize an oligonucleotide that spans the base or bases to be mutated and contains the mutated base or bases. The oligonucleotide is hybridized to complementary single stranded nucleic acid and second strand synthesis is primed from the oligonucleotide. The double-stranded nucleic acid is prepared for transformation into host cells, such as *E. coli* or other prokaryotes and yeast or other eukaryotes. Standard screening and vector amplification protocols are used to identify mutant sequences and obtain high yields.

Similarly, deletions and/or insertions of sagA genes may be constructed by any of a variety of known methods. For example, the gene may be digested with restriction enzymes and/or nucleases and be religated such that sequences are deleted, added, or substituted. Similarly, a variety of transposons and other insertional elements may be used to make recombinants having deletions and insertions. Thus, in one example, a sagA mutant containing a Ω insertional element in a sagA gene can be made as is known in the art. Other means of generating variant sequences, also known in the art, may be employed (for examples see Sambrook et al., supra, and Ausubel et al., supra). Moreover, verification of variant sequences is typically accomplished by restriction enzyme mapping, sequence analysis, and hybridization. Variants that encode a polypeptide that elicits an immunogenic response specific to a SLS polypeptide are particularly useful in the context of this invention.

As noted above, the present invention provides isolated or purified SLS polypeptides, peptides, or variants thereof as those terms have been previously defined herein. In one aspect, these isolated or purified materials may be obtained from a host cell expressing a recombinant nucleic acid that encodes SLS peptides that may be isolated from the host cell. The SLS peptides of the present invention may be purified by a variety of standard methods with or without a protease treatment or polyacrylamide electrophoresis step, and/or may be isolated from organisms other than *streptococci* that have been engineered to express an isolated sagA nucleic acid. For example, a SLS polypeptide of the present invention can be isolated by, among other methods, culturing suitable host and vector systems to produce a native SLS polypeptide or a peptide fusion using recombinant DNA methods (discussed further herein). Using these methods SLS may be engineered for export from the host cell, retained within the host cell, for example, within inclusion bodies, or integrated into the surface of host cell. When engineered for export, a supernatant from a culture of the host cell can be used to isolate exported SLS polypeptides. When integrated into the surface, SLS polypeptides may be obtained by protease treatment to obtain a crude surface peptide fraction. When expressed in inclusion bodies, SLS proteins, fusion polypeptides and the like may be obtained by a variety of purification procedures. For example, a SLS-containing extract can be applied to a suitable purification matrix such as a SLS antibody bound to a suitable support. Alternatively, anion or cation exchange resins, gel filtration or affinity, hydrophobic or reverse phase chromatography may be employed in order to purify the protein. The SLS polypeptide may also be concentrated using commercially available protein concentration filters, such as an Amicon or Millipore Pellicon ultrafiltration unit, or by vacuum dialysis.

In one example of isolating SLS polypeptides or peptides by recombinant methods, an isolated nucleic acid encoding a SLS polypeptide, peptide, or variants thereof may be expressed as a hexahistidine (6×His)-tagged molecule, permitting purification on a nickel-chelating matrix. Alternatively, other tags may be used, including FLAG® (DYKDDDDK, SEQ ID NO: 7) and GST. The associated tag may then be removed in the last step of purification, for example, for certain vectors, 6×His-tagged proteins may be incubated with thrombin, resulting in cleavage of a recognition sequence between the tag and the SLS polypeptide (e.g., pET vectors from Invitrogen, Carlsbad, Calif.).

It is well known in the art that certain vectors (e.g., pUC) can be used for producing multiple copies of a nucleotide molecule of interest as well as being useful for genetic manipulation techniques (e.g., site-directed mutagenesis; see Sambrook et al., supra). In certain aspects, preferably used are nucleic acid expression constructs. The nucleic acid expression construct includes transcriptional promoter/enhancer elements operably linked to an isolated nucleic acid molecule encoding a SLS polypeptide of interest. The nucleic acid expression construct may be composed of deoxyribonucleic acids ("DNA"), ribonucleic acids ("RNA"), or a combination of the two (e.g., a DNA-RNA chimera). Optionally, the nucleic acid expression construct may include a polyadenylation sequence or one or more restriction enzyme sites. Additionally, depending on the host cell chosen and the expression vector employed, other genetic elements such as an origin of replication, additional nucleic acid restriction enzyme sites, enhancers, sequences conferring inducibility of transcription, and genes encoding proteins suitable for use as selectable or identifiable markers, may also be incorporated into the nucleic acid expression construct described herein.

The manipulation and expression of sagA genes can be accomplished by culturing host cells containing a nucleic acid expression construct capable of expressing the sagA encoding nucleic acid molecule. Such vectors or vector constructs include either synthetic or cDNA-derived nucleic acid molecules or genomic DNA fragments encoding the SLS polypeptides, which are operably linked to suitable transcriptional or translational regulatory elements. Suitable regulatory elements within the expression vector can be derived from a variety of sources, including bacterial, fungal, viral, mammalian, insect, or plant genes. Selection of appropriate regulatory elements is dependent on the host cell chosen, and can be readily accomplished by one of ordinary skill in the art in light of the present specification and knowledge in the art. Exemplary regulatory elements include, for example, a transcriptional promoter and enhancer or RNA polymerase binding sequence, a transcriptional terminator, and a ribosomal binding sequence with a translation initiation signal.

Nucleic acid molecules that encode any of the SLS polypeptides, peptides, or variants thereof described above can be expressed by a wide variety of prokaryotic and eukaryotic host cells, including bacterial, mammalian, yeast or other fungi, viral, insect, and plant cells. The selection of a host cell may also assist the production of post-transitionally modified SLS polypeptides, depending upon the desires of the user. Methods for transforming or transfecting such cells to express nucleic acids are well known in the art (see, e.g., Itakura et al., U.S. Pat. No. 4,704,362; Hinnen et al., *PNAS* USA 75:1929–1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al., *Molecular Cloning: A Laboratory Manual*, $2^{nd}$ edition, Cold Spring Harbor Laboratory Press, 1989; for plant cells see Czako and Marton, *Plant Physiol.* 104: 1067–1071, 1994; Paszkowski et al., *Biotech.* 24:387–392, 1992).

Bacterial host cells suitable for carrying out the present invention include, without limitation, numerous strains of *E. coli*, as well as various strains of *M. leprae, M. tuberculosis, M. bovis, B. subtilis, Salmonella typhimurium,* and various species within the genera *Pseudomonas, Streptomyces,*

Streptococcus, and Staphylococcus, as well as many other bacterial species well known to one of ordinary skill in the art.

Bacterial expression vectors preferably comprise a promoter, which functions in the host cell, one or more selectable phenotypic markers, and a bacterial origin of replication. Representative promoters include the β-lactamase (penicillinase) and lactose promoter system (see Chang et al., Nature 275:615, 1978), the T7 RNA polymerase promoter (Studier et al., Meth. Enzymol. 185:60–89, 1990), the lambda promoter (Elvin et al., Gene 87:123–126, 1990), the trp promoter (Nichols and Yanofsky, Meth. in Enzymology 101:155, 1983) and the tac promoter (Russell et al., Gene 20:231, 1982). Representative selectable markers include various antibiotic resistance markers such as the kanamycin or ampicillin resistance genes. Many plasmids suitable for transforming host cells are well known in the art, including among others, pBR322 (see Bolivar et al., Gene 2:95, 1977), the pUC plasmids pUC18, pUC19, pUC118, pUC119 (see Messing, Meth. in Enzymology 101:20–77, 1983; Vieira and Messing, Gene 19:259–268, 1982), and pNH8A, pNH16a, pNH18a, and Bluescript M13 (Stratagene, La Jolla, Calif.). In one particular embodiment of this invention exemplified in Example 7, a 346 bp isolated nucleic acid encoding a Spa polypeptide was ligated into a pCR2.1-TOPO vector and expressed in E. coli.

Fungal host cells suitable for carrying out the present invention include, among others, Saccharomyces pombe, Saccharomyces cerevisiae, the genera Pichia or Kluyveromyces and various species of the genus Aspergillus (McKnight et al., U.S. Pat. No. 4,935,349). Suitable expression vectors for yeast and fungi include, among others, YCp50 (ATCC No. 37419) for yeast, and the amdS cloning vector pV3 (Turnbull, Bio/Technology 7:169, 1989), YRp7 (Struhl et al., Proc. Natl. Acad. Sci. USA 76:1035–1039, 1978), YEp13 (Broach et al., Gene 8:121–133, 1979), pJDB249 and pJDB219 (Beggs, Nature 275:104–108, 1978) and derivatives thereof.

Preferred promoters for use in yeast include promoters from yeast glycolytic genes (Hitzeman et al., J. Biol. Chem. 255:12073–12080, 1980; Alber and Kawasaki, J. Mol. Appl. Genet. 1:419–434, 1982) or alcohol dehydrogenase genes (Young et al., in Genetic Engineering of Microorganisms for Chemicals, Hollaender et al. (eds.), p. 355, Plenum, N.Y., 1982; Ammerer, Meth. Enzymol. 101:192–201, 1983). Examples of useful promoters for fungi vectors include those derived from Aspergillus nidulans glycolytic genes, such as the adh3 promoter (McKnight et al., EMBO J. 4:2093–2099, 1985). The expression units may also include a transcriptional terminator. An example of a suitable terminator is the adh3 terminator (McKnight et al., ibid., 1985).

As with bacterial vectors, the yeast vectors will generally include a selectable marker, which may be one of any number of genes that exhibit a dominant phenotype for which a phenotypic assay exists to enable transformants to be selected. Preferred selectable markers include those that complement host cell auxotrophy, provide antibiotic resistance or enable a cell to utilize specific carbon sources, and include leu2 (Broach et al., ibid.), ura3 (Botstein et al., Gene 8:17, 1979), or his3 (Struhl et al., ibid.). Another suitable selectable marker is the cat gene, which confers chloramphenicol resistance on yeast cells.

Techniques for transforming fungi are well known in the literature, and have been described, for instance, by Beggs (ibid.), Hinnen et al. (Proc. Natl. Acad. Sci. USA 75:1929–1933, 1978), Yelton et al. (Proc. Natl. Acad. Sci. USA 81:1740–1747, 1984), and Russell (Nature 301:167–169, 1983). The genotype of the host cell may contain a genetic defect that is complemented by the selectable marker present on the expression vector. Choice of a particular host and selectable marker is well within the level of ordinary skill in the art in light of the present specification.

Protocols for the transformation of yeast are also well known to those of ordinary skill in the art. For example, transformation may be readily accomplished either by preparation of spheroplasts of yeast with DNA (see Hinnen et al., PNAS USA 75:1929, 1978) or by treatment with alkaline salts such as LiCl (see Itoh et al., J. Bacteriology 153:163, 1983). Transformation of fungi may also be carried out using polyethylene glycol as described by Cullen et al. (Bio/Technology 5:369, 1987).

Viral vectors include those that comprise a promoter that directs the expression of an isolated nucleic acid molecule that encodes a SLS polypeptide as described above. A wide variety of promoters may be utilized within the context of the present invention, including for example, promoters such as MoMLV LTR, RSV LTR, Friend MuLV LTR, adenoviral promoter (Ohno et al., Science 265: 781–784, 1994), neomycin phosphotransferase promoter/enhancer, late parvovirus promoter (Koering et al., Hum. Gene Therap. 5:457–463, 1994), Herpes TK promoter, SV40 promoter, metallothionein IIa gene enhancer/promoter, cytomegalovirus immediate early promoter, and the cytomegalovirus immediate late promoter. The promoter may also be a tissue-specific promoter (see e.g., WO 91/02805; EP 0,415,731; and WO 90/07936). In addition to the above-noted promoters, other viral-specific promoters (e.g., retroviral promoters (including those noted above, as well as others such as HIV promoters), hepatitis, herpes (e.g., EBV), and bacterial, fungal or parasitic-specific (e.g., malarial-specific) promoters may be utilized in order to target a specific cell or tissue which is infected with a virus, bacteria, fungus or parasite.

Thus, SLS polypeptides of the present invention may be expressed from a variety of viral vectors, including for example, herpes viral vectors (e.g., U.S. Pat. No. 5,288,641), adenoviral vectors (e.g., WO 94/26914, WO 93/9191; Kolls et al., PNAS 91(1):215–219, 1994; Kass-Eisler et al., PNAS 90(24):11498–502, 1993; Guzman et al., Circulation 88(6): 2838–48, 1993; Guzman et al., Cir. Res. 73(6):1202–1207, 1993; Zabner et al., Cell 75(2):207–216, 1993; Li et al., Hum Gene Ther. 4(4):403–409, 1993; Caillaud et al., Eur. J. Neurosci. 5(10):1287–1291, 1993; Vincent et al., Nat. Genet. 5(2):130–134, 1993; Jaffe et al., Nat. Genet. 1(5): 372–378, 1992; and Levrero et al., Gene 101(2):195–202, 1991), adenovirus-associated viral vectors (Flotte et al., PNAS 90(22):10613–10617, 1993), baculovirus vectors, parvovirus vectors (Koering et al., Hum. Gene Therap. 5:457–463, 1994), pox virus vectors (Panicali and Paoletti, PNAS 79:4927–4931, 1982; and Ozaki et al., Biochem. Biophys. Res. Comm. 193(2):653–660, 1993), and retroviruses (e.g., EP 0,415,731; WO 90/07936; WO 91/0285, WO 94/03622; WO 93/25698; WO 93/25234; U.S. Pat. No. 5,219,740; WO 93/11230; WO 93/10218. Within various embodiments, either the viral vector itself or a viral particle which contains the viral vector may be utilized in the methods and compositions described below.

Mammalian cells suitable for carrying out the present invention include, among others: PC12 (ATCC No. CRL1721), N1E-115 neuroblastoma, SK-N-BE(2)C neuroblastoma, SHSY5 adrenergic neuroblastoma, NS20Y and NG108-15 murine cholinergic cell lines, or rat F2 dorsal root ganglion line, COS (e.g., ATCC No. CRL 1650 or 1651), BHK (e.g., ATCC No. CRL 6281; BHK 570 cell line (deposited with the American Type Culture Collection under accession number CRL 10314), CHO (ATCC No. CCL 61), HeLa (e.g., ATCC No. CCL 2), 293 (ATCC No. 1573; Graham et al., *J. Gen. Virol.* 36:59–72, 1977) and NS-1 cells. Other mammalian cell lines may be used within the present invention, including Rat Hep I (ATCC No. CRL 1600), Rat Hep II (ATCC No. CRL 1548), TCMK (ATCC No. CCL 139), Human lung (ATCC No. CCL 75.1), Human hepatoma (ATCC No. HTB-52), Hep G2 (ATCC No. HB 8065), Mouse liver (ATCC No. CCL 29.1), NCTC 1469 (ATCC No. CCL 9.1), SP2/0-Ag14 (ATCC No. 1581), HIT-T15 (ATCC No. CRL 1777), and RINm 5AHT2B (Orskov and Nielson, *FEBS* 229(1):175–178, 1988).

Mammalian expression vectors for use in carrying out the present invention include a promoter capable of directing the transcription of a cloned gene or cDNA. Preferred promoters include viral promoters and cellular promoters. Viral promoters include the cytomegalovirus immediate early promoter (Boshart et al., *Cell* 41:521–530, 1985), cytomegalovirus immediate late promoter, SV40 promoter (Subramani et al., *Mol. Cell. Biol.* 1:854–864, 1981), MMTV LTR, RSV LTR, metallothionein-1, adenovirus E1a. Cellular promoters include the mouse metallothionein-1 promoter (Palmiter et al., U.S. Pat. No. 4,579,821), action promoters, a mouse $V_H$ promoter (Bergman et al., *Proc. Natl. Acad. Sci. USA* 81:7041–7045, 1983; Grant et al., *Nucl. Acids Res.* 15:5496, 1987) and a mouse $V_H$ promoter (Loh et al., *Cell* 33:85–93, 1983). The choice of promoter will depend, at least in part, upon the level of expression desired or the recipient cell line to be transfected.

Such nucleic acid expression vectors can also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Suitable polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nuc. Acids Res.* 9:3719–3730, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer. Expression vectors may also include sequences encoding the adenovirus VA RNAs. Suitable expression vectors can be obtained from commercial sources (e.g., Stratagene, La Jolla, Calif.).

Nucleic acid expression constructs comprising isolated sagA sequences may be introduced into cultured mammalian cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841–845, 1982), or DEAE-dextran mediated transfection (Ausubel et al. (eds.), *Current Protocols in Molecular Biology,* John Wiley and Sons, Inc., N.Y., 1987). See generally Sambrook et al. (supra). To identify cells that have stably integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. Preferred amplifiable selectable markers are the DHFR gene and the neomycin resistance gene. Selectable markers are reviewed by Thilly (*Mammalian Cell Technology*, Butterworth Publishers, Stoneham, Mass.).

Mammalian cells containing a suitable vector are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable, selectable marker the drug concentration may be increased in a stepwise manner to select for increased copy number of the cloned sequences, thereby increasing expression levels. Cells expressing the introduced sequences are selected and screened for production of the protein of interest in the desired form or at the desired level. Cells that satisfy these criteria can then be cloned and scaled up for production.

Numerous insect host cells known in the art can also be useful within the present invention, in light of the subject specification. For example, the use of baculoviruses as vectors for expressing heterologous DNA sequences in insect cells has been reviewed by Atkinson et al. (*Pestic. Sci.* 28:215–224, 1990).

Numerous plant host cells known in the art can also be useful within the present invention, in light of the subject specification. For example, the use of *Agrobacterium rhizogenes* as vectors for expressing genes in plant cells has been reviewed by Sinkar et al., *J. Biosci. (Bangalore)* 11:47–58, 1987.

Upon expression of the SLS polypeptides or variants thereof in the host cells, the polypeptide or peptide may be preliminarily released and/or isolated from the host cell utilizing methods such as those discussed previously herein.

As noted above, depending on the host cell in which one desires to express a SLS polypeptide, an isolated nucleic acid encoding the polypeptide is introduced into an expression vector comprising a promoter that is active in the host cell. Other components of the expression unit such as transcribed but not translated sequences at the ends of the coding region may also be selected according to the particular host utilized. In some cases, it may be necessary to introduce artificially an intervening sequence to ensure high-level expression. Expression can be monitored by SDS-PAGE and staining, if expression levels are sufficiently high. Additionally, if the SLS polypeptide is produced with a tag, detection by anti-tag antibody may be carried out and if produced with no tag, detection by anti-SLS antibody that does not recognize homologous proteins of the host may be employed. Further, any method known in the art for protein identification may be utilized to this end (e.g., a high resolution electrophoretic method or 2D electrophoresis).

III. Antibodies

In another aspect, the SLS polypeptides, peptides, and variants thereof of the present invention are utilized to prepare antibodies specific for an epitope present on SLS polypeptides provided herein. Accordingly, the present invention also provides such antibodies. In preferred embodiments the antibodies bind to specific neutralizing epitopes present on a SLS peptide. Within the context of the present invention, the term "antibodies" includes polyclonal antibodies, monospecific antibodies, monoclonal antibodies, anti-idiotypic antibodies, fragments thereof such as $F(ab')_2$ and Fab fragments, and recombinantly or synthetically produced antibodies. Such antibodies incorporate the variable regions that permit a monoclonal antibody to specifically bind, which means an antibody is able to selectively bind to a peptide produced from a sagA sequence of this invention. "Specific for" refers to the ability of a protein (e.g., an antibody) to selectively bind a polypeptide or peptide encoded by a sagA (SLS-associated gene) nucleic acid molecule or a synthesized SagA of this invention. Association or "binding" of an antibody to a specific antigen generally involve electrostatic interactions, hydrogen bonding, Van der Waals interactions, and hydrophobic interactions. Any one of these or any combination thereof can play a role in the binding between an antibody and its antigen. Such an antibody generally associates with an antigen, such as SLS, with an affinity constant ($K_a$) of at least $10^4$, preferably at least $10^5$, more preferably at least $10^6$, still more preferably at least $10^7$ and most preferably at least $10^8$. Affinity constants may be determined by one of ordinary skill in the art using well-known techniques (see Scatchard, *Ann. N.Y. Acad. Sci.* 51:660–672, 1949). The affinity of a monoclonal antibody or antibody can be readily determined by one of ordinary skill in the art (see Scatchard, *Ann. N.Y. Acad. Sci.* 51:660–672, 1949).

In addition, the term "antibody," as used herein, includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies may be constructed using solid phase peptide synthesis, may be produced recombinantly, or may be obtained, for example, by screening combinatorial libraries consisting of variable heavy chains and variable light chains (Huse et al., *Science* 246:1275–1281 (1989)). These and other methods of making, for example, chimeric, humanized, CDR-grafted, single chain, and bifunctional antibodies are well known in the art (Winter and Harris, *Immunol. Today* 14:243, 1993; Ward et al., *Nature* 341:544, 1989; Harlow and Lane, *Antibodies: A Laboratory Manual*, Cold Spring Harbor Laboratory, New York, 1992; Borrabeck, *Antibody Engineering*, 2d ed., Oxford Univ. Press, 1995; Hilyard et al., *Protein Engineering: A practical approach*, IRL Press, 1992).

Polyclonal antibodies can be readily generated by one of ordinary skill in the art from a variety of warm-blooded animals such as horses, cows, goats, sheep, dogs, chickens, turkeys, rabbits, mice, or rats. Briefly, the desired SLS polypeptide, peptide, or variant thereof is utilized to immunize an animal through parenteral, intraperitoneal, intramuscular, intraocular, or subcutaneous injections. The immunogenicity of the SLS peptide of interest may be increased through the use of an adjuvant, such as alum and Freund's complete or incomplete adjuvant. Following several booster immunizations over a period of weeks, small samples of serum are collected and tested for reactivity to the desired SLS peptide. A preferred embodiment is an antibody specific for a peptide immunogen wherein the peptide immunogen comprises at least eight contiguous amino acids with at least 80% amino acid identity to SEQ ID NO:4 and comprises at least one streptolysin S epitope, wherein the antibody is polyclonal. Even more preferred is such a polyclonal antibody specific for at least one neutralizing epitope of SLS. Particularly preferred polyclonal immune sera give a signal that is at least three times greater than background. Once the titer of the animal has reached a plateau in terms of its reactivity to the SLS, larger quantities of polyclonal immune sera may be readily obtained either by weekly bleedings or by exsanguinating the animal.

Monoclonal antibodies may also be readily generated using well-known techniques (see U.S. Pat. No. RE 32,011, U.S. Pat. Nos. 4,902,614, 4,543,439, and 4,411,993; see also *Monoclonal Antibodies, Hybridomas: A New Dimension in Biological Analyses*, Plenum Press, Kennett, McKearn, and Bechtol (eds.), 1980, and *Antibodies: A Laboratory Manual*, Harlow and Lane (eds.), Cold Spring Harbor Laboratory Press, 1988). Briefly, in one embodiment, a subject animal such as a rat or mouse is injected with a desired protein or peptide. If desired, various techniques may be utilized in order to increase the resultant immune response generated by the protein, in order to develop greater antibody reactivity. For example, the desired protein or peptide may be coupled to another carrier protein (such as ovalbumin, keyhole limpet hemocyanin (KLH), or *E. coli* labile toxin B subunit) or through the use of adjuvants (such as alum or Freund's complete and incomplete adjuvant) and the like. A preferred embodiment is an antibody specific for a peptide immunogen wherein the peptide immunogen comprises at least eight contiguous amino acids with at least 80% amino acid identity to SEQ ID NO:4 and comprises at least one streptolysin S epitope, wherein the antibody is monoclonal. Even more preferred is such a monoclonal antibody specific for at least one neutralizing epitope of SLS.

The present invention also provides portions of a SLS polypeptide, SLS fusion proteins, and SLS cocktails comprising a second immunogen (e.g., M protein antigens). Fusion proteins are useful for several purposes, including the combining of two or more catalytic functions from separate polypeptide sources and for raising antibodies to epitopes. For raising antibodies to epitopes, as preferred embodiment is an antibody specific for a peptide immunogen linked to at least one additional amino acid sequence, wherein the peptide immunogen comprises at least eight contiguous amino acids with at least 80% amino acid identity to SEQ ID NO:4 and comprises at least one streptolysin S epitope. In one embodiment, the additional amino acid sequence comprises a carrier, such as ovalbumin, KLH, tetanus toxoid, diphtheria toxoid, albumin, lysozyme, gelatin, gamma globulin, cholera toxin B subunit, *E. coli* labile toxin B subunit, and flagellin. A typical protein for this purpose, without limitation, is KLH. Additionally, the present invention provides a non-naturally occurring SLS polypeptide or fusion protein that is synthetic or recombinant. More preferred embodiments of an additional amino acid sequence includes fusions that have been linked recombinantly or chemically. The additional amino acid sequence may optionally comprise another portion of the SLS polypeptide that is not naturally adjacent to the first segment, or comprise sequences from a non-SLS polypeptide, such as M protein, Spa, or any combination thereof. In one embodiment, the at least one additional amino acid sequence comprises a second immunogen, wherein the second immunogen comprises an M protein of group A *streptococci*. In a preferred embodiment, the M protein is an amino-terminal portion or a C-repeat region. Also provided are nucleic acids and vectors encoding the aforementioned fusion polypeptides and host cells carrying the same.

Depending on the SLS peptide immunogen, fusion protein, or cocktail mix used to immunize a subject to elicit specific antibodies, the present invention contemplates the following antibodies and methods for making them. In preferred embodiment, when SLS is fused or mixed with an M protein, as described herein, and administered to a subject, the preferred antibodies include at least one antibody that is specific for a streptolysin S epitope and at least one antibody that is specific for a M protein epitope. Even more preferred are antibodies wherein the at least one antibody specific for the streptolysin S epitope is a neutralizing antibody and the at least one antibody specific for the M protein epitope is a serotype-specific opsonic antibody that is not tissue cross-reactive. In another more preferred embodiment, the antibodies include at least one antibody specific for the streptolysin S epitope is a neutralizing antibody and the at least one antibody specific for the M protein epitope is a mucosal antibody. In yet another more preferred embodiment, the antibodies include wherein the at least one antibody specific for the streptolysin S epitope is a neutralizing antibody and the at least one antibody specific for the M protein epitope comprises at least one mucosal antibody and at least one serotype-specific opsonic antibody that is not tissue cross-reactive.

Use of carrier proteins, fusion polypeptides, or chemical linkers is particularly advantageous when antibody is elicited against a SLS peptide comprising at least one SLS neutralizing epitope. For example, chemical coupling to a carrier protein is described in Example 2, where a synthetic 21 SLS amino acid sequence consisting essentially of SEQ ID NO:6 having a carboxy-terminus cysteine for linkage to KLH in order to produce neutralizing antibodies against an epitope contained within the SLS peptide. Thus, in one preferred embodiment the additional amino acid sequence was a single amino acid (in this case, without limitation, it was cysteine). Other suitable carrier proteins may be produced recombinantly and include, without limitation, tetanus toxoid, diphtheria toxoid, albumin (e.g., bovine serum), lysozyme (e.g., hen egg), gelatin, gamma globulin (e.g., bovine), B subunit of cholera toxin, B subunit of *E. coli* labile toxin, and flagellin. In a preferred embodiment, recombinantly linking a SLS peptide to a carrier protein will include an in-frame fusion of the peptide through a linker amino acid sequence of at least 2 amino acids in length, wherein the amino acids are encoded by a nucleic acid sequence forming a restriction enzyme recognition site. In other embodiments, the linker may be 3 to 35 amino acids, or 7 to 15 amino acids wherein 2 to 7 of the linker amino acids are hydrophobic amino acids.

The present invention also provides methods for eliciting an immune response against *streptococci*, comprising administering to a subject any SLS peptide immunogen described herein. The initial elicitation of an immune response may preferably be through enteral, parenteral, transdermal/transmucosal, or inhalation routes. Preferably the SLS peptide immunogens or peptide immunogen compositions described herein may further comprise an adjuvant, such as alum or complete or incomplete Freund's. Between one and three weeks after the initial immunization, the animal may be re-immunized with the preferred SLS polypeptide, peptide, or variant thereof, including chemical and recombinant fusion proteins. The animal may then be bled and the serum tested for binding to the desired SLS peptide immunogen using assays as described above. Additional immunizations may also be accomplished until the animal has reached a plateau in its reactivity to the desired SLS polypeptide, peptide, or variant thereof. The animal may then be given a final boost of the desired fusion protein or peptide, and three to four days later sacrificed. At this time, the spleen and lymph nodes may be harvested and disrupted into a single cell suspension by passing the organs through a mesh screen or by rupturing the spleen or lymph node membranes that encapsulate the cells. Within one embodiment, the red cells are subsequently lysed by the addition of a hypotonic solution and immediately followed by a return to isotonicity.

Within another embodiment, suitable cells for preparing monoclonal antibodies are obtained through the use of in vitro immunization techniques. Briefly, an animal is sacrificed, and the spleen and lymph node cells are removed. A single cell suspension is prepared, and the cells are placed into a culture containing a form of the polypeptide, peptide or variant thereof of interest that is suitable for generating an immune response as described above. Subsequently, the lymphocytes are harvested and fused as described below.

Cells that are obtained through the use of in vitro immunization or from an immunized animal as described above may be immortalized by transfection with a virus such as the Epstein-Barr Virus (EBV). (See Glasky and Reading, *Hybridoma* 8(4):377–389, 1989.) Alternatively, within a preferred embodiment, the harvested spleen and/or lymph node cell suspensions are fused with a suitable myeloma cell in order to create a "hybridoma" which secretes monoclonal antibodies. Suitable myeloma lines are preferably defective in the construction or expression of antibodies, and are additionally syngeneic with the cells from the immunized animal. Many such myeloma cell lines are well known in the art and may be obtained from sources such as the American Type Culture Collection (ATCC), Rockville, Md. (see *Catalogue of Cell Lines & Hybridomas,* $6^{th}$ ed., ATCC, 1988). Representative myeloma lines include the following without limitation: for humans, UC 729-6 (ATCC No. CRL 8061), MC/CAR-Z2 (ATCC No. CRL 8147), and SKO-007 (ATCC No. CRL 8033); for mice, SP2/0-Ag14 (ATCC No. CRL 1581), and P3X63Ag8 (ATCC No. TIB 9); and for rats, Y3-Ag1.2.3 (ATCC No. CRL 1631), and YB2/0 (ATCC No. CRL 1662). Particularly preferred fusion lines include NS-1 (ATCC No. TIB 18) and P3X63-Ag 8.653 (ATCC No. CRL 1580), which may be utilized for fusions with mouse, rat, or human cell lines. Fusion between the myeloma cell line and the cells from the immunized animal can be accomplished by a variety of methods, including the use of polyethylene glycol (PEG) (see *Antibodies: A Laboratory Manual,* Harlow and Lane, supra) or electrofusion. (See Zimmerman and Vienken, *J. Membrane Biol.* 67:165–182, 1982.)

Following the fusion, the cells are placed into culture plates containing a suitable medium, such as RPMI 1640 or DMEM (Dulbecco's Modified Eagles Medium, JRH Biosciences, Lenexa, Kans.). The medium may also contain additional ingredients, such as Fetal Bovine Serum (FBS, e.g., from Hyclone, Logan, Utah, or JRH Biosciences), thymocytes that were harvested from a baby animal of the same species as was used for immunization, or agar to solidify the medium. Additionally, the medium should contain a reagent which selectively allows for the growth of fused spleen and myeloma cells. Particularly preferred is the use of HAT medium (hypoxanthine, aminopterin, and thymidine) (Sigma Chemical Co., St. Louis, Mo.). After about seven days, the resulting fused cells or hybridomas may be screened in order to determine the presence of antibodies which recognize the desired antigen. Following several clonal dilutions and reassays, hybridoma producing antibodies that bind to the protein of interest can be isolated.

Other techniques may also be utilized to construct monoclonal antibodies. (See Huse et al., "Generation of a Large Combinational Library of the Immunoglobulin Repertoire in Phage Lambda," *Science* 246:1275–1281, 1989; see also Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. USA* 86:5728–5732, 1989; see also Alting-Mees et al., "Monoclonal Antibody Expression Libraries: A Rapid Alternative to Hybridomas," *Strategies in Molecular Biology* 3:1–9, 1990; these references describe a commercial system available from Stratagene, La Jolla, Calif., which enables the production of antibodies through recombinant techniques). Briefly, mRNA is isolated from a B cell population and utilized to create heavy and light chain immunoglobulin cDNA expression libraries in the λIMMUNOZAP(H) and λIMMUNOZAP(L) vectors. These vectors may be screened individually or co-expressed to form Fab fragments or antibodies (see Huse et al., supra; see also Sastry et al., supra). Positive plaques can subsequently be converted to a non-lytic plasmid, which allows high level expression of monoclonal antibody fragments from E. coli.

Similarly, antibodies may also be constructed utilizing recombinant DNA techniques to incorporate the variable regions of a gene that encodes a specifically binding antibody. The construction of these antibodies can be readily accomplished by one of ordinary skill in the art given the disclosure provided herein. (See Larrick et al., *Biotechnology* 7:934–938, 1989; Riechmann et al., *Nature (London)* 332:323–327, 1988; Roberts et al., *Nature (London)* 328: 731–734, 1987; Verhoeyen et al., *Science* 239:1534–1536, 1988; Chaudhary et al., *Nature (London)* 339:394–397, 1989; see also U.S. Pat. No. 5,132,405). Briefly, in one embodiment, DNA segments encoding the desired SLS peptide of interest-specific antigen binding domains are amplified from hybridomas that produce a specifically binding monoclonal antibody, and are inserted directly into the genome of a cell that produces human antibodies. (See Verhoeyen et al., supra; see also Reichmann et al., supra). This technique allows the antigen-binding site of a specifically binding mouse or rat monoclonal antibody to be transferred into a human antibody. Such antibodies are preferable for therapeutic use in humans because they are not as antigenic as rat or mouse antibodies.

In an alternative embodiment, genes that encode the variable region from a hybridoma producing a monoclonal antibody of interest are amplified using oligonucleotide primers for the variable region. These primers may be synthesized by one of ordinary skill in the art, or may be purchased from commercially available sources. For instance, primers for mouse and human variable regions including, among others, primers for $V_{Ha}$, $V_{Hb}$, $V_{Hc}$, $V_{Hd}$, $C_{H1}$, $V_L$ and $C_L$ regions, are available from Stratagene (La Jolla, Calif.). These primers may be utilized to amplify heavy or light chain variable regions, which may then be inserted into vectors such as IMMUNOZAP™(H) or IMMUNOZAP™(L) (Stratagene), respectively. These vectors may then be introduced into E. coli for expression. Utilizing these techniques, large amounts of a single-chain polypeptide containing a fusion of the $V_H$ and $V_L$ domains may be produced (see Bird et al., *Science* 242:423–426, 1988).

Monoclonal antibodies and other antibodies can be produced in a number of host systems, including tissue cultures, bacteria, eukaryotic cells, plants and other host systems known in the art.

Once suitable antibodies or antibodies have been obtained, they may be isolated or purified by many techniques well known to those of ordinary skill in the art (see *Antibodies: A Laboratory Manual*, Harlow and Lane, supra). Suitable techniques include peptide or protein affinity columns, HPLC or RP-HPLC, purification on protein A or protein G columns, or any combination of these techniques. Within the context of the present invention, the term "isolated" as used to define antibodies or antibodies means "substantially free of other blood components." For example, anti-SLS peptide antibodies were affinity purified as described in Example 4.

The antibodies of the present invention have many uses. For example, antibodies can be utilized in flow cytometry to identify cells bearing such a protein. Briefly, in order to detect the SLS polypeptide, peptide, or variant thereof of interest on cells, the cells are incubated with a labeled monoclonal antibody specific for the protein of interest, followed by detection of the presence of bound antibody. Labels suitable for use within the present invention are well known in the art including, among others, flourescein isothiocyanate (FITC), phycoerythrin (PE), horse radish peroxidase (HRP), and colloidal gold. Particularly preferred for use in flow cytometry is FITC, which may be conjugated to purified antibody according to the method of Keltkamp in "Conjugation of Fluorescein Isothiocyanate to Antibodies. I. Experiments on the Conditions of Conjugation," *Immunology* 18:865–873, 1970. (See also Keltkamp, "Conjugation of Fluorescein Isothiocyanate to Antibodies. II. A Reproducible Method," *Immunology* 18:875–881, 1970; Goding, "Conjugation of Antibodies with Fluorochromes: Modification to the Standard Methods," *J. Immunol. Methods* 13:215–226, 1970.) The antibodies can also be used to target drugs against *streptococci*, to diagnose infection by these bacteria, or for treating an infection caused thereby.

IV. Diagnostic Applications

Nucleic acid molecules can be used to detect the presence of *streptococci* or expression of the sagA gene in a biological sample. Such probe molecules include double-stranded nucleic acid molecules comprising the nucleotide sequence of SEQ ID NOS:1, 3 or 5, or a fragment thereof, as well as single-stranded nucleic acid molecules having the complement of the nucleotide sequence of SEQ ID NOS:1, 3 or 5, or a fragment thereof. Probe molecules may be DNA, cDNA, RNA, oligonucleotides, and the like.

Preferred probes bind with regions of the sagA gene that have a low sequence similarity to comparable regions in other streptococcal proteins. For example, suitable probes will bind with at least one portion of the nucleotide sequence of SEQ ID NO:1. As used herein, the term "portion" refers to at least eight or more nucleotides.

In a basic assay, a single-stranded probe molecule is incubated with RNA, isolated from a biological sample, under conditions of temperature and ionic strength that promote base pairing between the probe and target sagA RNA species. After separating unbound probe from hybridized molecules, the amount of hybrids is detected.

Well-established hybridization methods of RNA detection include northern analysis and dot/slot blot hybridization (see, e.g., Ausubel, pages 4–1 to 4–27, 1995; Wu et al. (eds.), *Methods in Gene Biotechnology*, pages 225–239, CRC Press, Inc., 1997). Nucleic acid probes can be detectably labeled with radioisotopes such as $^{32}P$ or $^{35}S$. Alternatively, sagA RNA can be detected with a nonradioactive hybridization method (see, for example, Isaac (ed.), *Protocols for Nucleic Acid Analysis by Nonradioactive Probes* (Humana Press, Inc. 1993)). Typically, nonradioactive detection is achieved by enzymatic conversion of chromogenic or chemiluminescent substrates. Illustrative nonradioactive moieties include biotin, fluorescein, and digoxigenin.

Numerous diagnostic procedures take advantage of the polymerase chain reaction (PCR) to increase sensitivity of detection methods. Standard techniques for performing PCR are well-known (see, generally, Mathew (ed.), *Protocols in Human Molecular Genetics*, Humana Press, Inc., 1991; White (ed.), *PCR Protocols: Current Methods and Applications*, Humana Press, Inc., 1993; Cotter (ed.), *Molecular Diagnosis of Cancer*, Humana Press, Inc., 1996; Hanausek and Walaszek (eds.), *Tumor Marker Protocols,* Humana Press, Inc., 1998; Lo (ed.), *Clinical Applications of PCR,* Humana Press, Inc., 1998; and Meltzer (ed.), *PCR in Bioanalysis,* Humana Press, Inc., 1998). Preferably, PCR primers are designed to amplify a portion of the sagA gene that has a low sequence similarity to other streptococcal proteins. In addition suitable primers include those designed to amplify portions of a sagA gene encoding an immunogenic epitope of SEQ ID NOS: 2, 4 or 6.

One variation of PCR for diagnostic assays is reverse transcriptase-PCR (RT-PCR). RT-PCR has been used to detect dissemination of prostate cancer cells to metastatic sites in prostate cancer patients (Moreno et al., *Cancer Res.* 52:6110, 1992; Vessella et al., *Proc. Am. Assoc. Can. Res.* 33:2367, 1992; Olsson et al., *Urologic Clinics of North America* 24:367, 1997; Robbins, International Publication No. WO 97/39139). In the RT-PCR technique, RNA is isolated from a biological sample, reverse transcribed to cDNA, and the cDNA is incubated with sagA primers (see, e.g., Wu et al. (eds.), *Methods in Gene Biotechnology,* pages 15–28, CRC Press, Inc., 1997). PCR is then performed and the products are analyzed using standard techniques.

Briefly, a biological sample is obtained from a sample for RNA preparation. If the test material contains a variety of biological materials, then the sample may be layered onto a Ficoll-Hypaque density gradient and centrifuged in order to separate some of the biological materials. RNA may then be isolated from the sample using, for example, the gunadinium-thiocyanate cell lysis procedure described above. Alternatively, a solid-phase technique can be used to isolate mRNA from a cell lysate. A reverse transcription reaction can be primed with the isolated RNA using random oligonucleotides, short homopolymers of dT, or sagA antisense oligomers. Oligo-dT primers offer the advantage that various mRNA nucleotide sequences are amplified that can provide control target sequences. SagA sequences are amplified by the polymerase chain reaction using two flanking oligonucleotide primers that are typically 20 bases in length.

PCR amplification products may be detected using a variety of approaches. For example, PCR products can be fractionated by gel electrophoresis and visualized by ethidium bromide staining. Alternatively, fractionated PCR products may be transferred to a membrane, hybridized with a detectably-labeled sagA probe, and examined by autoradiography. Additional alternative approaches include the use of digoxigenin-labeled deoxyribonucleic acid triphosphates to provide chemiluminescence detection, and the C-TRAK colorimetric assay.

Another approach for detection of sagA expression is cycling probe technology (CPT), in which a single-stranded DNA target binds with an excess of DNA-RNA-DNA chimeric probe to form a complex, the RNA portion is cleaved with RNAase H, and the presence of cleaved chimeric probe is detected (see, e.g., Beggs et al., *J. Clin. Microbiol.* 34:2985, 1996; Bekkaoui et al., *Biotechniques* 20:240, 1996). Alternative methods for detection of sagA sequences may utilize approaches such as nucleic acid sequence-based amplification (NASBA), cooperative amplification of templates by cross-hybridization (CATCH), and the ligase chain reaction (LCR) (see, e.g., Marshall et al., U.S. Pat. No. 5,686,272 (1997), Dyer et al., *J. Virol. Methods* 60:161, 1996; Ehricht et al., *Eur. J. Biochem.* 243:358, 1997; and Chadwick et al., *J. Virol. Methods* 70:59, 1998). Other standard methods are known to those of skill in the art. Various additional diagnostic approaches are well-known to those of skill in the art (see, e.g., Mathew (ed.), *Protocols in Human Molecular Genetics,* Humana Press, Inc., 1991; Coleman and Tsongalis, *Molecular Diagnostics,* Humana Press, Inc., 1996; and Elles, *Molecular Diagnosis of Genetic Diseases,* Humana Press, Inc., 1996).

The present invention also contemplates kits for performing a diagnostic assay for sagA gene expression or for the presence of *streptococci* in a biological sample. Such kits comprise nucleic acid probes comprising a portion of the nucleotide sequence of SEQ ID NOS:3 or 5, or a fragment thereof, or nucleic acids encoding a peptide according to SEQ ID NOS:4 or 6, or variants thereof. Probe molecules may be DNA, cDNA, RNA, oligonucleotides, and the like. Kits may comprise nucleic acid primers for performing PCR. Preferably, such a kit contains all the necessary elements to perform a nucleic acid diagnostic assay described above. A kit will comprise one or more containers, in which one container comprises a sagA probe or primer, and a second container comprises one or more reagents capable of indicating the presence of sagA sequences. Examples of such indicator reagents include detectable labels such as radioactive labels, fluorochromes, chemiluminescent agents, and the like. A kit will also comprise written material describing the use of such sagA probes and primers for detection of sagA gene expression or the presence of streptoccocci cells. The written material can be applied directly to a container, or the written material may be provided in the form of a packaging insert.

The present invention further contemplates the use of anti-SLS antibodies to screen biological samples in vitro for the presence of SLS polypeptides, peptides, or variants thereof. In one type of in vitro assay, anti-SLS antibodies are used in liquid phase. For example, the presence of SLS in a biological sample can be tested by mixing the biological sample with a trace amount of labeled SLS and an anti-SLS antibody under conditions that promote binding between SLS and its antibody. Complexes of SLS and anti-SLS in the sample can be separated from the reaction mixture by contacting the complex with an immobilized protein which binds with the antibody, such as an Fc antibody or Staphylococcus protein A. The concentration of SLS in the biological sample will be inversely proportional to the amount of labeled SLS bound to the antibody and directly related to the amount of labeled SLS that is free. Alternatively, in vitro assays can be performed in which anti-SLS antibody is bound to a solid-phase carrier to detect the presence of SLS. For example, antibody can be attached to a polymer, such as aminodextran, in order to link the antibody to an insoluble support such as a polymer-coated bead, a plate or a tube. Other suitable in vitro assays will be readily apparent to those of skill in the art.

Immunochemical detection may be performed by contacting a biological sample with an anti-SLS antibody and then contacting the biological sample with a detectably labeled molecule that binds to the antibody. For example, the detectably labeled molecule can comprise an antibody moiety that binds to anti-SLS antibody. Alternatively, the anti-SLS antibody can be conjugated with avidin/streptavidin (or biotin) and the detectably labeled molecule can comprise biotin (or avidin/streptavidin). Numerous variations of this basic technique are well known to those of skill in the art.

Alternatively, an anti-SLS antibody can be conjugated with a detectable label to form an anti-SLS immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail herein. The detectable label can be a radioisotope that is detected by autoradiography. Isotopes that are particularly useful for the purpose of the present invention are $^3$H, $^{125}$I, $^{131}$I, $^{35}$S and $^{14}$C.

Anti-SLS immunoconjugates can also be labeled with a fluorescent compound. The presence of a fluorescently labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, fluorescamine, and the like.

Alternatively, anti-SLS immunoconjugates can be detectably labeled by coupling an antibody component to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-SLS immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-SLS immunoconjugates can be detectably labeled by linking an anti-SLS antibody component to an enzyme. When the anti-SLS-enzyme conjugate is incubated in the presence of the appropriate substrate, the enzyme moiety reacts with the substrate to produce a chemical moiety which can be detected, for example, by spectrophotometric, fluorometric, or visual means. Examples of enzymes that can be used to detectably label polyspecific immunoconjugates include, without limitation, β-galactosidase, glucose oxidase, peroxidase and alkaline phosphatase.

Those of skill in the art will know of other suitable labels that can be employed in accordance with the present invention. The binding of marker moieties to anti-SLS antibodies can be accomplished using standard techniques known to the art. Typical methodology in this regard is described by Kennedy et al., *Clin. Chim. Acta* 70:1, 1976; Schurs et al., *Clin. Chim. Acta* 81:1, 1977; Shih et al., *Int'l J. Cancer* 46:1101, 1990; Stein et al., *Cancer Res.* 50:1330, 1990; and Coligan, supra. Moreover, the convenience and versatility of immunochemical detection can be enhanced by using anti-SLS antibodies that have been conjugated with avidin, streptavidin, and biotin (see, e.g., Wilchek et al. (eds.), "Avidin-Biotin Technology," *Methods In Enzymology*, 184, Academic Press, 1990; Bayer et al., "Immunochemical Applications of Avidin-Biotin Technology," in *Methods In Molecular Biology* 10, Manson (ed.), pages 149–162, The Humana Press, Inc., 1992).

Methods for performing immunoassays are well-established (see, e.g., Cook and Self, "Monoclonal Antibodies in Diagnostic Immunoassays," in *Monoclonal Antibodies: Production, Engineering, and Clinical Application*, Ritter and Ladyman (eds.), pages 180–208, Cambridge University Press, 1995; Perry, "The Role of Monoclonal Antibodies in the Advancement of Immunoassay Technology," in *Monoclonal Antibodies: Principles and Applications*, Birch and Lennox (eds.), pages 107–120, Wiley-Liss, Inc., 1995; and Diamandis, *Immunoassay*, Academic Press, Inc., 1996).

The present invention also contemplates kits for performing an immunological diagnostic assay for SLS polypeptides, peptides, or variants thereof. Such kits comprise one or more containers, in which one container comprises an anti-SLS antibody or antibody fragment. A second container may comprise one or more reagents capable of indicating the presence of SLS antibody or antibody fragments. Examples of such indicator reagents include detectable labels, such as a radioactive label, a fluorescent label, a chemiluminescent label, an enzyme label, a bioluminescent label, colloidal gold, and the like. A kit will also comprise written material describing the use of SLS antibodies and antibody fragments for detection of SLS protein. The written material can be applied directly to a container or the written material can be provided in the form of a packaging insert.

V. Therapeautic Compositions and Methods

The discovery of a new protective antigen of the SLS toxin from group A *streptococci* enables another aspect of this invention, which is the provision of therapeutic compositions to protect against or to alter the course of streptococcal infections. As used herein, to "protect against infections" means to prevent, reduce the likelihood of, or ameliorate the pathogenic effects of an infection caused by *streptococci*. In certain embodiments, a composition for protecting an animal from a *streptococcus* infection comprising a biologically acceptable diluent and an effective amount of a an immunizing agent is selected from a peptide comprised of at least 21 amino acids of the carboxy-terminus of a streptolysin S polypeptide from a *streptococcus* species wherein the polypeptide has at least 80% amino acid identity to SEQ ID NOS:4 or 6; a peptide that is an immunogen having an neutralizing epitope; a host cell expressing a peptide having an opsonic epitope; and an antibody that specifically binds to a peptide with an epitope that may or may not be opsonic. An SLS immunizing agent includes the aforementioned antibodies, polypeptides, peptides, or variants thereof whether naturally occurring, synthetic, or produced by a host cells expressing a recombinant expression vector containing a nucleic acid sequence encoding a SLS immunizing agent, which proteins are reactive with antibodies raised against the isolated SLS polypeptides, peptides, or variants thereof of the present invention.

In a typical embodiment, the therapeutic composition containing a SLS immunizing agent comprises an SLS antigen that is protective against multiple *streptococci* serotypes. In a more typical embodiment the therapeutic composition contains an opsonic epitope that is cross protective against group A *streptococci*. Such a composition is expected to be considerably less complex than previous compositions comprised of M-protein or derivatives thereof, such as compositions where limited amino-terminal fragments of different M proteins were linked in tandem to evoke protective immune responses against each serotype represented in the vaccine. While such an approach has the advantage of limiting the amount of M protein contained in a vaccine or therapeutic composition, a large number of combinations must be provided because each M protein fragment is type-specific. This necessitates the development of relatively complex vaccines to prevent the majority of streptococcal infections in a given population or geographic region. In contrast, the SLS immunizing agents of the present invention may be used to provide broad protection and/or may be used in combination with M-proteins and other peptides to enhance the effectiveness of protection provided by either protein alone.

In this aspect, the present invention provides compositions and methods comprising one or more of the above-described SLS immunizing agents in combination with one or more pharmaceutically, biologically, or physiologically acceptable excipients, carriers, binders or diluents. As used herein, the terms excipient, carrier, binder and diluent are not mutually exclusive and may be used interchangeably. In certain embodiments, the compositions of the instant invention may further comprise an adjuvant, such as alum, Freund's, and the like. Compositions containing SLS antigens can be used to elicit or enhance an immune response in a recipient animal, which is preferably a human being and preferably elicits or enhances a protective or partially protective immunity against *streptococcus*, or against a host cell expressing an immunogen comprised of a SLS immunizing agent of the present invention. In yet other embodiments, the SLS immunizing agent is conjugated to a carrier protein, such as KLH. Compositions containing antibodies that specifically bind to an SLS peptide epitope may be used to diagnose or treat infections caused by *streptococci*, and in particular anti-SLS antibody, such as humanized antibody, will be useful in the treatment of acute streptococcal infections. Further, therapeutic compositions of the present invention should preferably be stable for several months and capable of being produced and maintained under sterile conditions.

The compositions can be sterile either by preparing them under an aseptic environment and/or they can be terminally sterilized using methods available in the art. Many pharmaceuticals are manufactured to be sterile and this criterion is defined by the USP XXII <1211>. Sterilization in this embodiment may be accomplished by a number of means accepted in the industry and listed in the USP XXII <1211>, including gas sterilization, ionizing radiation or filtration. Sterilization may be maintained by what is termed aseptic processing, defined also in USP XXII <1211>. Acceptable gases used for gas sterilization include ethylene oxide. Acceptable radiation types used for ionizing radiation methods include gamma, for instance from a cobalt 60 source and electron beam. A typical dose of gamma radiation is 2.5 MRad. When appropriate, filtration may be accomplished using a filter with suitable pore size, for example 0.22 μm and of a suitable material, for instance Teflon®. The term "USP" refers to U.S. Pharmacopeia (Rockville, Md.).

Preferably, the carrier or adjuvant are nontoxic to recipients at the dosages and concentrations employed. Ordinarily, the preparation of such compositions entails combining the SLS immunizing agent of this invention with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Examples of adjuvants include Freund's adjuvant and, for humans, preferably alum or aluminum hydroxide.

It will be evident in light of the present specification to those in the art that the amount and frequency of administration can be optimized in clinical trials, and will depend upon such factors as the disease or disorder to be treated, the degree of immune inducement, enhancement, or protection required, and many other factors.

In one embodiment, the therapeutic composition is administered orally, and a SLS immunizing agent of the invention is taken up by cells, such as cells located in the lumen of the gut. Other typical routes of administration include, without limitation, enteral, parenteral, transdermal/transmucosal, and inhalation. The term enteral, as used herein, is a route of administration in which the agent is absorbed through the gastrointestinal tract or oral mucosa, including oral, rectal, and sublingual. The term parenteral, as used herein, describes administration routes that bypass the gastrointestinal tract, including intraarterial, intradermal, intramuscular, intranasal, intraocular, intraperitoneal, intravenous, subcutaneous, submucosal, and intravaginal injection or infusion techniques. The term transdermal/transmucosal, as used herein, is a route of administration in which the agent is administered through or by way of the skin, including topical. The term inhalation encompasses techniques of administration in which an agent is introduced into the pulmonary tree, including intrapulmonary or transpulmonary. The SLS compositions of the present invention may be prepared and administered as a liquid solution or prepared as a solid form (e.g., lyophilized), which may be administered in solid form, or resuspended in a solution in conjunction with administration.

Depending upon the application, quantities of SLS immunizing agent in the composition will vary generally from about 0.1 μg to 1000 mg, typically from about 1 μg to 100 mg, more typically from about 10 μg to 10 mg, and usually from about 100 μg to 1 mg, in combination with the biologically acceptable carrier and/or adjuvant. Booster immunizations may be given at 2–6 weeks intervals to maximize the immune response.

The SLS immunizing agents of this invention may also be used with immunological carriers in conjugate vaccines. Preferably, a beneficial carrier includes another polypeptide that is has immunostimulant and does not have immunosuppressive effects. Such immunological carriers may be used to elicit an increased immune response to the conjugated molecule. The sagA gene products of this invention may also be used as carriers (in conjugates or fusion polypeptides) in combination with other antigens so as to provide compositions providing further protection elicited by epitopes additional to those contained on SLS, for example, M protein polypeptides as described herein.

A further aspect of the present invention is protection from *streptococcus* infections by treatment of an animal, preferably a mammal, and most preferably a human with a therapeutic composition containing the SLS immunizing agent of the present invention. As used herein, "protection" means to prevent or to reduce the severity of a disease associated with a *streptococcus* infection. In a typical practice, the SLS immunizing agent of the present invention may provide protection against multiple serotypes of *streptococci*, and preferably protection will be provided against multiple stereotypes of group A *streptococci.*

Another aspect of the present invention is therapeutic methods for protecting an animal against a *streptococcus* infection that includes the step of administering to the animal at least one of the aforementioned therapeutic compositions. Typically, administering a therapeutic composition containing SLS immunizing agent elicits antibodies in the animal and more preferably opsonic antibodies. Similarly, administering a composition containing an immunizing agent comprising an antibody raised against SLS antigen(s) may provide opsonic antibodies that facilitate a phagocytic response in an animal. In a preferred embodiment, protection is provided against multiple serotypes of *streptococcus*. In a related embodiment, the therapeutic composition is administered by at least one route selected from topical, oral, intranasal, intramuscular, subcutaneous, and vascular. In another preferred embodiment, the therapeutic method is used with a human.

From the foregoing it will be appreciated that, although specific embodiments of the invention have been described herein for purposes of illustration, various modifications may be made without deviating from the spirit and scope of the invention. Accordingly, the invention is not limited except as by the appended claims.

EXAMPLE 1

Synthesys and Coupling of SLS and Immunization of Rabbits

Full length SagA (streptolysin S) is a prepropolypeptide having 53 amino acids (SEQ ID NO:2) and the 30 amino acids of the carboxy-terminus of the prepropolypeptide encompass the SLS propolypeptide (SEQ ID NO:4). The nine (9) amino-terminal amino acids of the SagA propeptide includes seven cysteines and two threonines (FIG. 1). Without wishing to be bound by theory, we surmised the amino-terminal amino acids of the streptolysin S propeptide may be involved in the cytolytic activity of this polypeptide. Thus, a SLS peptide immunogen was synthesized (Research Genetics, Inc., Huntsville, Ala.), which includes amino acids 10–30 of the putative propeptide, which is referred to as S-SLS(10–30) (SEQ ID No.:6, FIG. 1). In addition, the prepropolypeptide and the propolypeptide were synthesized, although the propolypeptide was difficult to make due to the high number of amino-terminal cysteines. A carboxy-terminal cysteine was added to S-SLS(10–30), which is referred to as S-SLS(10–30)C, to facilitate coupling of the peptide to KHL using a bifunctional cross-linker. The conjugated polypeptide, S-SLS(10–30)C-KLH was purified as previously described (see Dale and Beachey, *J. Exp. Med.* 163: 1191, 1986).

Three New Zealand white rabbits were each immunized with 300 µg of S-SLS(10–30)C-KLH that had been emulsified in complete Freund's adjuvant (Dale and Beachey, supra). The same dose of peptide in saline was given in booster injections at 4 and 8 weeks following the initial inoculation. Serum was obtained before the first injection and at 2-week intervals thereafter.

EXAMPLE 2

Affinity Purification of SLS Antibodies

Anti-peptide antibodies were affinity purified from immune rabbit serum over a column containing S-SLS (10–30)C peptide covalently linked to Affi-Gel 10 (Bio-Rad Laboratories, Inc., Hercules, Calif.) as previously described (Dale and Beachey, *J. Exp. Med.* 163:1191, 1986). Control antibodies were purified from rabbit antiserum raised against a synthetic peptide of type 2 streptococcal M protein using a column containing SM2(1–35)C peptide (Dale et al., *Vaccine* 14:944, 1996). Total protein concentrations were determined and both samples were adjusted to contain 1.2 mg/ml of antibody.

EXAMPLE 3

Enzyme-Linked Immunosorbent Assays

ELISAs were performed on preimmune and immune rabbit sera using S-SLS(10–30)C as the solid-phase antigen, as previously described (Dale et al., *J Exp Med* 151:1026, 1980). Preimmune and immune sera from all three rabbits were assayed for the presence of antibodies against the S-SLS(10–30)C peptide by ELISA. The preimmune sera did not contain detectable levels of anti-peptide antibodies, while the immune sera obtained after the second injection (weeks 6–13) all had ELISA titers ranging from 12,800 to 51,200 (data not shown). All three rabbits responded equally to the S-SLS(10–30)C-KLH conjugate.

EXAMPLE 4

Antibody-Mediated Inhibition of SLS Activity on Blood Agar Plates

Type 24 group A *streptococci* were streaked onto blood agar that contained 5% preimmune or immune serum against S-SLS(10–30)C peptide. β-hemolysis was observed after overnight growth at 37° C. The immune serum significantly inhibited β hemolysis, while the preimmune serum had no effect (FIG. 2).

EXAMPLE 5

Antibody-Mediated Inhibition of SLS-Induced Hemolysys in Solution

Quantitative assays of hemoglobin release from sheep red blood cells (SRBC) were performed to determine the specificity and sensitivity of the antibody-mediated inhibition of SLS activity. Type 24 group A *streptococci* (Vaughn strain) were grown to late log-phase in Todd-Hewitt broth (THB) containing 0.2% yeast extract. Culture supernatant was collected after centrifugation and stored in aliquots at −80° C. Bacterial cell-associated SLS activity was detected using freshly grown type 24 *streptococci* that were collected, washed, and resuspended in PBS to an O.D. of 1.0. Inhibition of SLS-induced hemolysis by antibodies that specifically recognize SLS was assayed by mixing 0.5 ml of culture supernatant diluted 1:2 in PBS, 0.5 ml of either preimmune or immune rabbit serum diluted 1:2 in PBS, and 1.0 ml of a 2% suspension of washed sheep red blood cells (SRBC) in PBS. The reaction mixtures were incubated at 37° C. for 45 minutes and centrifuged (1000×g). The absorbance at 540 nm was measured to determine the release of hemoglobin. Cell-associated SLS activity was similarly detected using 1 ml of freshly grown, washed bacteria instead of diluted culture supernatant. In some experiments, cholesterol (500 µg/ml) or trypan blue (13 µg/ml) were added to the reaction mixtures to specifically inhibit the lytic activity of SLO or SLS, respectively (Betschel et al., supra). Peptide inhibition of the anti-SLS antibody was performed by preincubating the rabbit anti-sera with varying concentrations of S-SLS (10–30)C peptide at 370° C. for 45 minutes prior to adding the serum to the reaction mixture.

Preincubation of *streptococci* growth supernatant with rabbit immune serum against S-SLS(10–30)C peptide before addition to SRBC completely inhibited hemolysis of SRBC (Experiment #1 of Table 1). In a separate experiment, complete inhibition of hemolysis by the immune serum was also observed when the reaction mixture contained cholesterol, which specifically inhibits SLO-mediated hemolysis, but has no effect on the activity of SLS (Experiment #2 of Table 1). The bacterial cell-associated hemolytic activity was similarly inhibited in the presence of immune serum, but not pre-immune serum, and the addition of cholesterol had no effect on the level of inhibition (Experiment #3 of Table 1). These results indicate that the neutralizing activity of the immune serum was specific for SLS that was either cell-associated or in the supernatant. In addition, preincubation of the growth supernatant with trypan blue resulted in complete inhibition of hemolysis, indicating that all of the hemolytic activity observed with this preparation was actually mediated by SLS (data not shown).

In subsequent studies, serial dilutions of anti-SLS peptide immunogen antibody were used to determine the potency of the neutralizing antibodies (Table 2). Dilution of the immune serum to 1:8 in the reaction mixture resulted in 97% inhibition of hemolysis, while dilution to 1:16 produced approximately 50% inhibition. No inhibitory activity was seen at a final dilution of 1:32 (Table 2).

TABLE 1

Inhibition of Streptolysin S Activity by Anti-S-SLS(10–30)C Peptide Antibody

| | Reaction Mixture[a] | | | | % Inhibition |
|---|---|---|---|---|---|
| | SLS Source | Test Serum | Cholesterol | O.D.$_{450}$ | of hemolysis |
| Experiment #1 | Supernatant | Preimmune | None | 1.64 | — |
| | | Immune[b] | None | 0.05 | 97.0 |
| Experiment #2 | Supernatant | Preimmune | None | 2.66 | — |
| | | Immune | None | 0.07 | 97.4 |
| | | Preimmune | 0.5 mg/ml | 2.70 | — |
| | | Immune | 0.5 mg/ml | 0.07 | 97.4 |
| | | None (THB)[c] | None | 2.66 | — |
| Experiment #3 | Bacterial cells | Preimmune | None | 1.97 | — |
| | | Immune | None | 0.01 | 99.5 |
| | | Preimmune | 0.5 mg/ml | 2.3 | — |
| | | Immune | 0.5 mg/ml | 0.01 | 99.6 |

[a]Reaction mixtures contained 0.5 ml of serum diluted 1:2 before use, 1 ml of a 2% washed suspension of sheep red blood cells, and 0.5 ml of either growth supernatant diluted 1:2 or bacterial cell pellet diluted to an O.D. of 1.0.
[b]Immune = 9 week serum.
[c]THB = Todd-Hewitt broth.

TABLE 2

Titration of Anti-S-SLS(10–30)C Peptide Antibody Activity

| Serum | Final Serum Dilution | O.D.$_{450}$ | % Inhibition of hemolysis |
|---|---|---|---|
| Preimmune | 1:8 | 1.64 | — |
| 9 week | 1:8 | 0.05 | 97 |
| Preimmune | 1:16 | 1.85 | — |
| 9 week | 1:16 | 0.76 | 59 |
| Preimmune | 1:32 | 1.82 | — |
| 9 week | 1:32 | 1.85 | 0 |

EXAMPLE 6

Specificity of Anti-SLS Antibodies

Peptide inhibition assays were performed to assure that the SLS neutralizing antibodies in the immune serum were specific for SLS. Preincubation of the immune serum with either 250 μg/ml or 50 μg/ml of S-SLS(10–30)C reversed the neutralizing activity of the immune serum to levels approaching that observed with pre-immune serum (Table 3). Preincubation of fresh THB with 250 μg/ml of the S-SLS(53) (synthetic SEQ ID NO:2), S-SLS(30) (synthetic SEQ ID NO:4), or S-SLS(10–30)C resulted in no hemolysis of SRBC (data not shown), indicating that the peptide itself does not possess hemolytic activity.

Additionally, affinity purified antibodies (i.e., purified over a S-SLS(10–30)C column) were tested for neutralizing activity. Control antibodies specific for a synthetic peptide of type 2 streptococcal M protein were purified over a SM2 (1–35)C column. The purified antibody preparations were adjusted to contain 1.2 mg/ml of total protein and ELISA titers were determined using the respective peptides as the solid-phase antigens. The titer of the affinity purified antibodies were 12,800 each, both of which were comparable to the respective titers of the immune sera (data not shown). The affinity purified anti-S-SLS(10–30)C antibodies neutralized 95% of the SLS-mediated hemolysis, while the control SM2 antibodies had no effect on hemolysis (Table 4). Thus, anti-SLS antibodies are responsible for inhibiting SLS-induced SRBC lysis.

TABLE 3

Specificity of Anti-S-SLS(10–30)C Peptide Antibody Activity by Peptide Inhibition

| Serum | S-SLS(10–30)C added[a] | O.D.$_{450}$ | % Total hemolysis |
|---|---|---|---|
| Preimmune | None | 1.47 | 100 |
| | 250 ug/ml | 1.45 | 99.0 |
| Immune[b] | None | 0.06 | 4.0 |
| | 250 ug/ml | 1.35 | 92.0 |
| | 50 ug/ml | 1.17 | 80.0 |

[a]Serum was preincubated with the synthetic peptide at 37° for 45 min. prior to adding to the reaction mixture.
[b]Immune = 9 weeks.

TABLE 4

Inhibitory Activity of Affinity Purified Anti-S-SLS(10–30)C Peptide Antibody

| Antibody | O.D.$_{450}$ | % Inhibition of Hemolysis[a] |
|---|---|---|
| Preimmune serum | 1.59 | — |
| Immune serum (14 week) | 0.03 | 98 |
| Purified anti-S-SLS(10–30)C[b] | 0.08 | 95 |
| Purified anti-S-M2(1–35)C[c] | 1.80 | 0 |

[a]Reaction mixtures contained growth supernatant from type 24 streptococci diluted 1:4, 2% SRBC, and 0.5 mg/ml cholesterol to inhibit SLO activity.
[b]Specific antibodies were eluted from an affinity column containing the synthetic peptide S-SLS(10–30)C. Antibody was used at a concentration of 1.2 mg/ml.
[c]Control antibodies were purified from rabbit serum raised against a synthetic peptide of type 2 M protein, S-M2(1–35)C. Antibody was used at a concentration of 1.2 mg/ml.

The invention claimed is:

1. A composition, comprising a pharmaceutically acceptable carrier and a peptide immunogen for eliciting an immune response in a subject, wherein the amino acid sequence of the peptide immunogen is at least 80% identical to the amino acid sequence set forth in SEQ ID NO: 6, wherein the peptide immunogen has at least one streptolysin S epitope, and wherein the peptide immunogen elicits an antibody that neutralizes hemolytic activity of streptolysin S.

2. A composition comprising a pharmaceutically acceptable carrier and a peptide immunogen for eliciting an immune response in a subject, wherein the peptide immunogen consists of the amino acid sequence set forth in SEQ ID NO:6.

3. The composition of claim 1 wherein the amino acid sequence of the peptide immunogen is at least 90% identical to the amino acid sequence set forth in SEQ ID NO: 6.

4. The composition according to claim 1 wherein the amino acid sequence of the peptide immunogen is at least 95% identical to the amino acid sequence set forth in SEQ ID NO: 6.

5. The composition according to any one of claims 1, 3, and 4 further comprising a second immunogen that comprises a hybrid multivalent M polypeptide.

6. The composition according to claim 5 wherein the peptide immunogen is linked to the hybrid multivalent M polypeptide.

7. The composition according to claim 6 wherein the peptide immunogen and the multivalent M polypeptide are linked recombinantly or chemically.

8. The composition according to claim 5 wherein the peptide immunogen and multivalent M polypeptide are recombinant or synthetic.

9. The composition according to any one of claims 1, 3, and 4 wherein the subject is a human or an animal.

10. The composition according to any one of claims 1, 3, and 4 further comprising an adjuvant.

11. The composition according to claim 10 wherein the adjuvant is alum or Freund's.

12. The composition according to claim 1 wherein the composition is sterile.

13. The composition according to claim 2 comprising a second immunogen that comprises a hybrid multivalent M polypeptide.

14. The composition according to claim 13, wherein the peptide immunogen is linked to the hybrid multivalent M polypeptide.

15. The composition according to claim 14, wherein the peptide immunogen and the multivalent M polypeptide are linked recombinantly or chemically.

16. The composition according any one of claims 13–15 wherein the peptide immunogen and multivalent M polypeptide an recombinant or synthetic.

17. The composition according to either claim 2 or claim 13 wherein the subject is a human or an animal.

18. The composition according to either claim 2 or claim 13 further comprising an adjuvant.

19. The composition according to claim 18, wherein the adjuvant is alum or Freund's.

20. The composition according to either claim 2 or claim 13, wherein the composition is sterile.

21. The composition according to claim 2, wherein the peptide immunogen elicits an anti-streptolysin S neutralizing antibody.

* * * * *

UNITED STATES PATENT AND TRADEMARK OFFICE
CERTIFICATE OF CORRECTION

PATENT NO. : 7,160,547 B2 Page 1 of 1
APPLICATION NO. : 10/268336
DATED : January 9, 2007
INVENTOR(S) : James B. Dale It is certified that error appears in the above-identified patent and that said Letters Patent is hereby corrected as shown below:

<u>Column 48</u>
Line 14, "an" should read as --are--.

Signed and Sealed this

Twelfth Day of August, 2008

JON W. DUDAS
*Director of the United States Patent and Trademark Office*